United States Patent
Swanson et al.

(10) Patent No.: US 7,371,233 B2
(45) Date of Patent: *May 13, 2008

(54) COOLED PROBES AND APPARATUS FOR MAINTAINING CONTACT BETWEEN COOLED PROBES AND TISSUE

(75) Inventors: David K. Swanson, Campbell, CA (US); Huy D. Phan, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 455 days.

This patent is subject to a terminal disclaimer.

(21) Appl. No.: 10/784,316

(22) Filed: Feb. 19, 2004

(65) Prior Publication Data

US 2005/0187544 A1   Aug. 25, 2005

(51) Int. Cl.
  *A61B 18/18* (2006.01)
  *A61B 5/04* (2006.01)
(52) U.S. Cl. .................. 606/41; 128/898; 600/373
(58) Field of Classification Search ............ 606/32–35, 606/37–42, 45–50; 607/96, 100–102, 115, 607/116, 122; 600/374; 128/898
  See application file for complete search history.

(56) References Cited

U.S. PATENT DOCUMENTS

| | | |
|---|---|---|
| 3,805,793 A | 4/1974 | Wright |
| 4,326,529 A | 4/1982 | Doss et al. |
| 4,682,596 A | 7/1987 | Bales |
| 4,685,466 A | 8/1987 | Rau |
| 4,736,749 A | 4/1988 | Lundback |
| 4,832,048 A | 5/1989 | Cohen |
| 5,055,100 A | 10/1991 | Olsen |
| 5,085,657 A | 2/1992 | Ben-Simhon |
| 5,224,944 A | 7/1993 | Elliott |
| 5,281,213 A | 1/1994 | Milder et al. |
| 5,292,320 A | 3/1994 | Brown et al. |
| 5,318,262 A | 6/1994 | Adams |
| 5,330,518 A | 7/1994 | Neilson et al. |
| 5,334,193 A | 8/1994 | Nardella |
| 5,336,170 A | 8/1994 | Salerno |
| 5,348,554 A | 9/1994 | Imran |
| 5,383,876 A | 1/1995 | Nardella |
| 5,398,683 A | 3/1995 | Edwards |
| 5,409,483 A | 4/1995 | Campbell et al. |
| 5,443,470 A | 8/1995 | Stern et al. |
| 5,450,846 A | 9/1995 | Goldreyer |
| 5,496,271 A | 3/1996 | Burton et al. |

(Continued)

FOREIGN PATENT DOCUMENTS

EP   1125549 A2   5/1980

(Continued)

OTHER PUBLICATIONS

PCT International Search Report dated Mar. 4, 3005 for PCT application No. PCT/US2004/039143.

(Continued)

*Primary Examiner*—Henry M. Johnson, III
(74) *Attorney, Agent, or Firm*—Vista IP Law Group, LLP

(57) ABSTRACT

Apparatus and methods for maintaining contact between tissue and cooled probes.

42 Claims, 10 Drawing Sheets

U.S. PATENT DOCUMENTS

| | | |
|---|---|---|
| 5,505,730 A | 4/1996 | Edwards |
| 5,545,193 A | 8/1996 | Fleischman |
| 5,569,241 A | 10/1996 | Edwards |
| 5,569,242 A | 10/1996 | Lax |
| 5,571,088 A * | 11/1996 | Lennox et al. ............ 604/96.01 |
| 5,575,772 A | 11/1996 | Lennox |
| 5,582,609 A | 12/1996 | Swanson |
| 5,584,872 A | 12/1996 | LaFontaine |
| 5,609,151 A | 3/1997 | Mulier |
| 5,613,659 A | 3/1997 | Hong |
| 5,624,392 A | 4/1997 | Saab |
| 5,630,837 A | 5/1997 | Crowley |
| 5,637,090 A | 6/1997 | McGee |
| 5,637,884 A | 6/1997 | Yang |
| 5,673,695 A | 10/1997 | McGee |
| 5,676,693 A | 10/1997 | LaFontaine |
| 5,683,366 A | 11/1997 | Eggers |
| 5,688,267 A | 11/1997 | Panescu et al. |
| 5,697,536 A | 12/1997 | Eggers |
| 5,697,882 A | 12/1997 | Eggers |
| 5,697,927 A | 12/1997 | Imran et al. |
| 5,775,327 A | 7/1998 | Randolph et al. |
| 5,782,899 A | 7/1998 | Imran |
| 5,785,706 A | 7/1998 | Bednarek |
| 5,792,140 A | 8/1998 | Tu et al. |
| 5,797,903 A | 8/1998 | Swanson et al. |
| 5,797,905 A | 8/1998 | Fleischman |
| 5,800,482 A | 9/1998 | Pomeranz |
| 5,800,484 A | 9/1998 | Gough |
| 5,807,395 A | 9/1998 | Mulier et al. |
| 5,824,005 A | 10/1998 | Motamedi |
| 5,833,688 A | 11/1998 | Sieben et al. |
| 5,861,021 A | 1/1999 | Thome |
| 5,879,347 A | 3/1999 | Saadat |
| 5,879,348 A | 3/1999 | Owens |
| 5,891,134 A | 4/1999 | Goble et al. |
| 5,910,129 A | 6/1999 | Koblish |
| 5,913,854 A | 6/1999 | Maguire et al. |
| 5,938,659 A | 8/1999 | Tu et al. |
| 5,938,694 A | 8/1999 | Jaraczewski |
| 5,951,546 A | 9/1999 | Lorentzen |
| 5,957,922 A | 9/1999 | Imran |
| 5,961,490 A | 10/1999 | Adams |
| 5,961,513 A | 10/1999 | Swanson |
| 5,971,983 A | 10/1999 | Lesh |
| 6,002,968 A | 12/1999 | Edwards |
| 6,004,269 A | 12/1999 | Crowley et al. |
| 6,012,457 A | 1/2000 | Lesh |
| 6,015,407 A | 1/2000 | Rieb et al. |
| 6,017,338 A | 1/2000 | Brucket et al. |
| 6,023,638 A | 2/2000 | Swanson |
| 6,024,740 A | 2/2000 | Lesh |
| 6,032,077 A | 2/2000 | Pomeranz |
| 6,032,672 A | 3/2000 | Taylor |
| 6,036,697 A | 3/2000 | DiCaprio |
| 6,048,329 A | 4/2000 | Thompson et al. |
| 6,053,912 A | 4/2000 | Panescu et al. |
| 6,053,937 A | 4/2000 | Edwards et al. |
| 6,068,653 A | 5/2000 | LaFontaine |
| 6,071,274 A | 6/2000 | Thompson |
| 6,071,279 A | 6/2000 | Whayne |
| 6,071,281 A | 6/2000 | Burnside |
| 6,076,012 A | 6/2000 | Swanson et al. |
| 6,115,626 A | 9/2000 | Whayne |
| 6,117,101 A | 9/2000 | Diederich |
| 6,142,994 A | 11/2000 | Swanson et al. |
| 6,159,207 A | 12/2000 | Yoon |
| 6,164,283 A | 12/2000 | Lesh |
| 6,168,594 B1 | 1/2001 | LaFontaine |
| 6,185,442 B1 | 2/2001 | Samson |
| 6,190,381 B1 | 2/2001 | Olsen et al. |
| 6,237,605 B1 | 5/2001 | Vaska et al. |
| 6,241,727 B1 | 6/2001 | Tu et al. |
| 6,258,087 B1 | 7/2001 | Edwards et al. |
| 6,264,654 B1 | 7/2001 | Swartz et al. |
| 6,270,493 B1 | 8/2001 | Lalonde et al. |
| 6,277,115 B1 | 8/2001 | Saadat |
| 6,280,441 B1 | 8/2001 | Ryan |
| 6,287,301 B1 | 9/2001 | Thompson |
| 6,290,699 B1 | 9/2001 | Hall et al. |
| 6,306,133 B1 | 10/2001 | Tu et al. |
| 6,308,104 B1 | 10/2001 | Taylor |
| 6,311,692 B1 | 11/2001 | Vaska et al. |
| 6,314,962 B1 | 11/2001 | Vaska et al. |
| 6,325,797 B1 | 12/2001 | Stewart |
| 6,364,876 B1 | 4/2002 | Erb et al. |
| 6,371,955 B1 | 4/2002 | Fuimaono |
| 6,394,948 B1 | 5/2002 | Borst et al. |
| 6,447,443 B1 | 9/2002 | Keogh et al. |
| 6,464,700 B1 | 10/2002 | Koblish et al. |
| 6,468,272 B1 | 10/2002 | Koblish |
| 6,475,179 B1 | 11/2002 | Wang |
| 6,485,489 B2 | 11/2002 | Teirstein et al. |
| 6,514,250 B1 | 2/2003 | Jahns et al. |
| 6,522,905 B2 | 2/2003 | Desai |
| 6,522,930 B1 | 2/2003 | Schaer et al. |
| 6,527,767 B2 | 3/2003 | Wang et al. |
| 6,529,756 B1 | 3/2003 | Phan et al. |
| 6,542,781 B1 | 4/2003 | Koblish et al. |
| 6,558,382 B2 | 5/2003 | Jahns et al. |
| 6,579,288 B1 | 6/2003 | Swanson et al. |
| 6,584,360 B2 | 6/2003 | Francischelli et al. |
| 6,645,202 B1 | 11/2003 | Pless et al. |
| 6,652,518 B2 * | 11/2003 | Wellman et al. ............... 606/41 |
| 6,663,622 B1 * | 12/2003 | Foley et al. ................... 606/34 |
| 6,706,038 B2 | 3/2004 | Francischelli et al. |
| 6,771,996 B2 | 8/2004 | Bowe et al. |
| 6,786,898 B2 | 9/2004 | Guenst |
| 6,814,731 B2 | 11/2004 | Swanson |
| 6,837,885 B2 | 1/2005 | Koblish et al. |
| 6,849,075 B2 * | 2/2005 | Bertolero et al. ............... 606/41 |
| 6,887,238 B2 | 5/2005 | Jahns et al. |
| 6,893,442 B2 | 5/2005 | Whayne |
| 6,939,350 B2 | 9/2005 | Phan |
| 7,020,531 B1 | 3/2006 | Colliou et al. |
| 7,077,842 B1 | 7/2006 | Cosman |
| 7,207,988 B2 * | 4/2007 | Leckrone et al. ............... 606/41 |
| 2001/0007071 A1 | 7/2001 | Koblish et al. |
| 2002/0002372 A1 | 1/2002 | Jahns et al. |
| 2002/0026187 A1 | 2/2002 | Swanson |
| 2003/0036754 A1 | 2/2003 | Erb |
| 2003/0060685 A1 | 3/2003 | Hauser |
| 2003/0069570 A1 | 4/2003 | Witzel et al. |
| 2003/0078575 A1 | 4/2003 | Jahns et al. |
| 2003/0078644 A1 | 4/2003 | Phan |
| 2003/0083655 A1 | 5/2003 | Van Wyk |
| 2003/0120268 A1 | 6/2003 | Bertolero et al. |
| 2003/0153905 A1 | 8/2003 | Edwards et al. |
| 2003/0167056 A1 | 9/2003 | Jahns et al. |
| 2003/0216724 A1 | 11/2003 | Jahns |
| 2004/0006336 A1 | 1/2004 | Swanson |
| 2004/0018467 A1 | 1/2004 | Tanaka et al. |
| 2004/0138522 A1 | 7/2004 | Haarstad |
| 2004/0153057 A1 * | 8/2004 | Davison ...................... 606/41 |
| 2004/0267192 A1 | 12/2004 | Weldon et al. |
| 2005/0019545 A1 | 1/2005 | Riebel |
| 2005/0019653 A1 | 1/2005 | Dahlberg |
| 2005/0049583 A1 | 3/2005 | Swanson |
| 2005/0059962 A1 | 3/2005 | Phan |
| 2005/0119648 A1 | 6/2005 | Swanson |
| 2005/0119649 A1 | 6/2005 | Swanson |
| 2005/0119654 A1 | 6/2005 | Swanson |
| 2005/0222564 A1 | 10/2005 | Plaza |

2005/0261673 A1 11/2005 Bonner et al.

FOREIGN PATENT DOCUMENTS

| EP | 0856292 A1 | 8/1998 |
|---|---|---|
| EP | 1169972 A1 | 1/2002 |
| WO | WO 97/10753 A1 | 3/1997 |
| WO | WO 99/48421 A1 | 9/1999 |
| WO | WO 00/56237 A2 | 9/2000 |
| WO | WO 01/58373 A1 | 8/2001 |
| WO | WO 02/17804 A2 | 3/2002 |
| WO | WO 03/024305 A1 | 3/2003 |
| WO | WO 04/093698 A1 | 11/2004 |

OTHER PUBLICATIONS

Final Office Action dated Aug. 14, 2007 for U.S. Appl. No. 10/395,021, filed Mar. 21, 2003 (9 pages).
Amendment dated Jun. 27, 2007 for U.S. Appl. No. 10/395,021, filed Mar. 21, 2003 (18 pages).
Non-Final Office Action dated Mar. 27, 2007 for U.S. Appl. No. 10/395,021, filed Mar. 21, 2003 (7 pages).
Amendment dated Jan. 23, 2007 for U.S. Appl. No. 10/395,021, filed Mar. 21, 2003 (21 pages).
Final Office Action dated Oct. 24, 2006 for U.S. Appl. No. 10/395,021, filed Mar. 21, 2003 (7 pages).
Amendment dated Aug. 15, 2006 for U.S. Appl. No. 10/395,021, filed Mar. 21, 2003 (14 pages).
Non-Final Office Action dated May 10, 2006 for U.S. Appl. No. 10/395,021, filed Mar. 21, 2003 (5 pages).
Amendment dated Apr. 12, 2006 for U.S. Appl. No. 10/395,021, filed Mar. 21, 2003 (14 pages).
Non-Final Office Action dated Apr. 10, 2006 for U.S. Appl. No. 10/395,021, filed Mar. 21, 2003 (5 pages).
Amendment dated Jan. 30, 2006 for U.S. Appl. No. 10/395,021, filed Mar. 21, 2003 (12 pages).
Non-Final Office Action dated Nov. 28, 2005 for U.S. Appl. No. 10/395,021, filed Mar. 21, 2003 (5 pages).
Amendment dated Oct. 17, 2005 for U.S. Appl. No. 10/395,021, filed Mar. 21, 2003 (12 pages).
Non-Final Office Action dated May 17, 2005 for U.S. Appl. No. 10/395,021, filed Mar. 21, 2003 (6 pages).
Amendment dated Apr. 6, 2005 for U.S. Appl. No. 10/395,021, filed Mar. 21, 2003 (11 pages).
Non-Final Office Action dated Dec. 7, 2004 for U.S. Appl. No. 10/395,021, filed Mar. 21, 2003 (6 pages).
Non-Final Office Action dated Jun. 14, 2007 for U.S. Appl. No. 10/727,149, filed Dec. 2, 2003 (6 pages).
Amendment dated Apr. 6, 2007 for U.S. Appl. No. 10/727,149, filed Dec. 2, 2003 (14 pages).
Final Office Action dated Jan. 9, 2007 for U.S. Appl. No. 10/727,149, filed Dec. 2, 2003 (7 pages).
Amendment dated Dec. 7, 2006 for U.S. Appl. No. 10/727,149, filed Dec. 2, 2003 (14 pages).
Non-Final Office Action dated Sep. 15, 2006 for U.S. Appl. No. 10/727,149, filed Dec. 2, 2003 (5 pages).
Amendment dated Apr. 12, 2006 for U.S. Appl. No. 10/727,149, filed Dec. 2, 2003 (14 pages).
Non-Final Office Action dated Jan. 13, 2006 for U.S. Appl. No. 10/727,149, filed Dec. 2, 2003 (13 pages).
Amendment dated Aug. 20, 2007 for U.S. Appl. No. 10/727,096, filed Dec. 2, 2003 (14 pages).
Non-Final Office Action dated May 18, 2007 for U.S. Appl. No. 10/727,096, filed Dec. 2, 2003 (8 pages).
Amendment dated Apr. 27, 2007 for U.S. Appl. No. 10/727,096, filed Dec. 2, 2003 (11 pages).
Final Office Action dated Feb. 7, 2007 for U.S. Appl. No. 10/727,096, filed Dec. 2, 2003 (8 pages).
Amendment dated Nov. 9, 2006 for U.S. Appl. No. 10/727,096, filed Dec. 2, 2003 (14 pages).
Non-Final Office Action dated Jul. 13, 2006 for U.S. Appl. No. 10/727,096, filed Dec. 2, 2003 (10 pages).
Amendment dated May 4, 2006 for U.S. Appl. No. 10/727,096, filed Dec. 2, 2003 (12 pages).
Final Office Action dated Mar. 7, 2006 for U.S. Appl. No. 10/727,096, filed Dec. 2, 2003 (8 pages).
Amendment dated Dec. 3, 2005 for U.S. Appl. No. 10/727,096, filed Dec. 2, 2003 (10 pages).
Non-Final Office Action dated Aug. 8, 2005 for U.S. Appl. No. 10/727,096, filed Dec. 2, 2003 (6 pages).
PCT International Search Report dated Aug. 2, 2004 for PCT Application No. PCT/US2004/005883, Applicant Scimed Life Systems (now Boston Scientific Scimed), forms PCT/ISA 210 and 220, (10 pages).
PCT Written Opinion dated Aug. 2, 2004 for PCT Application No. PCT/US2004/005883, Applicant Scimed Life Systems (now Boston Scientific Limited), forms PCT/ISA 234 and PCT/IPEA 237, (10 pages).
EP Office Action, dated Mar. 22, 2006 for Application No. 04715649.2, Applicant Boston Scientific Limited, (3 pages).
Response to EP Office Action, dated Mar. 22, 2006, submitted on Jul. 21, 2006, for Application No. 04715649.2, Applicant Boston Scientific Limited, (11 pages).
Communication under Rule 51(4) EPC, dated Dec. 22, 2006, for Application No. 04715649.2, Applicant Boston Scientific Limited, (5 pages).

* cited by examiner

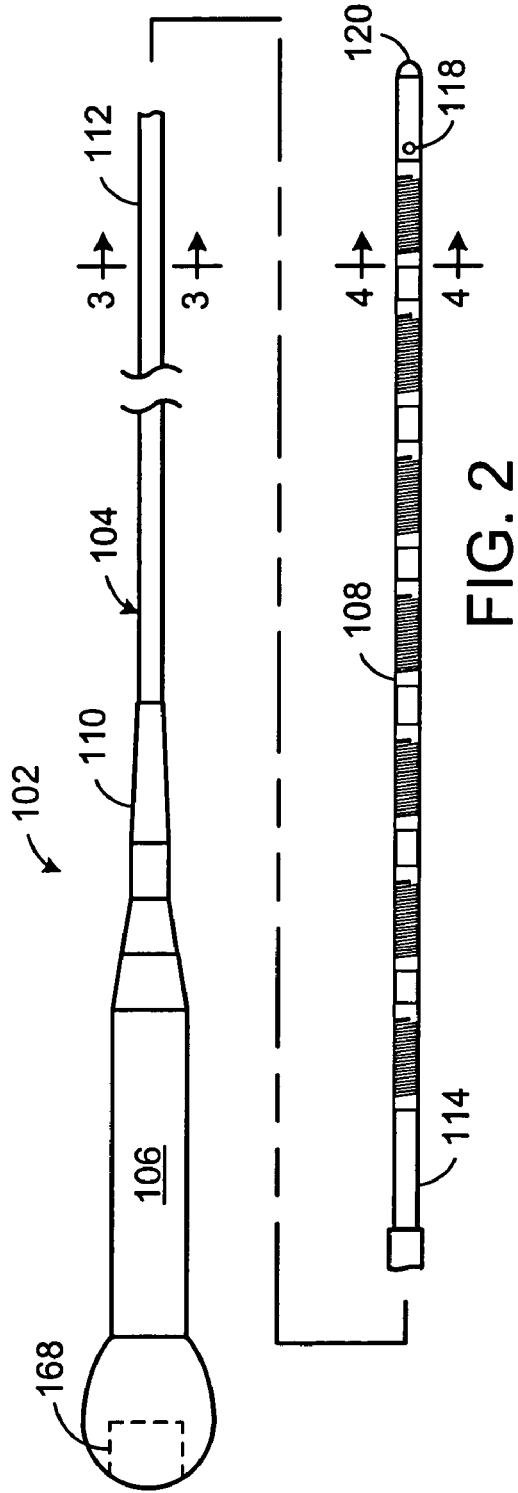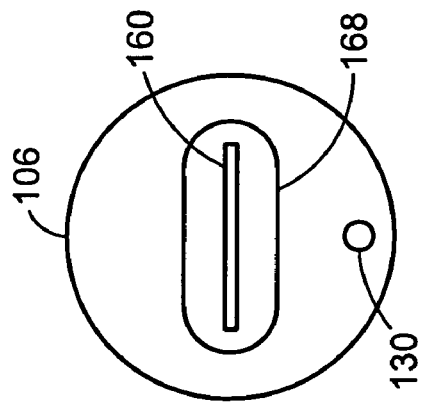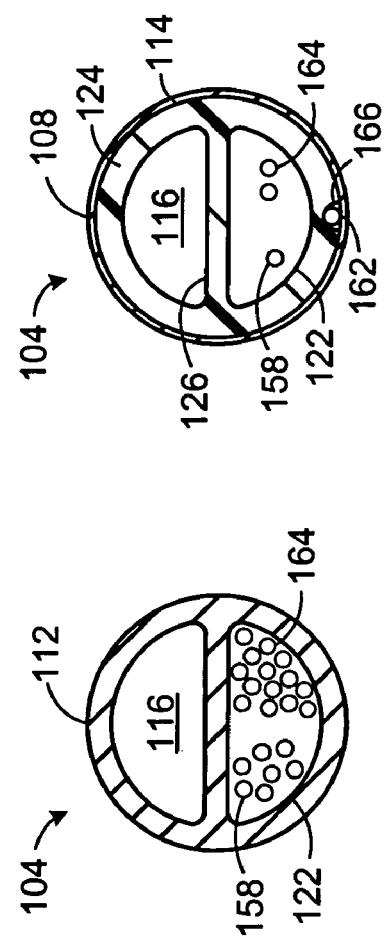

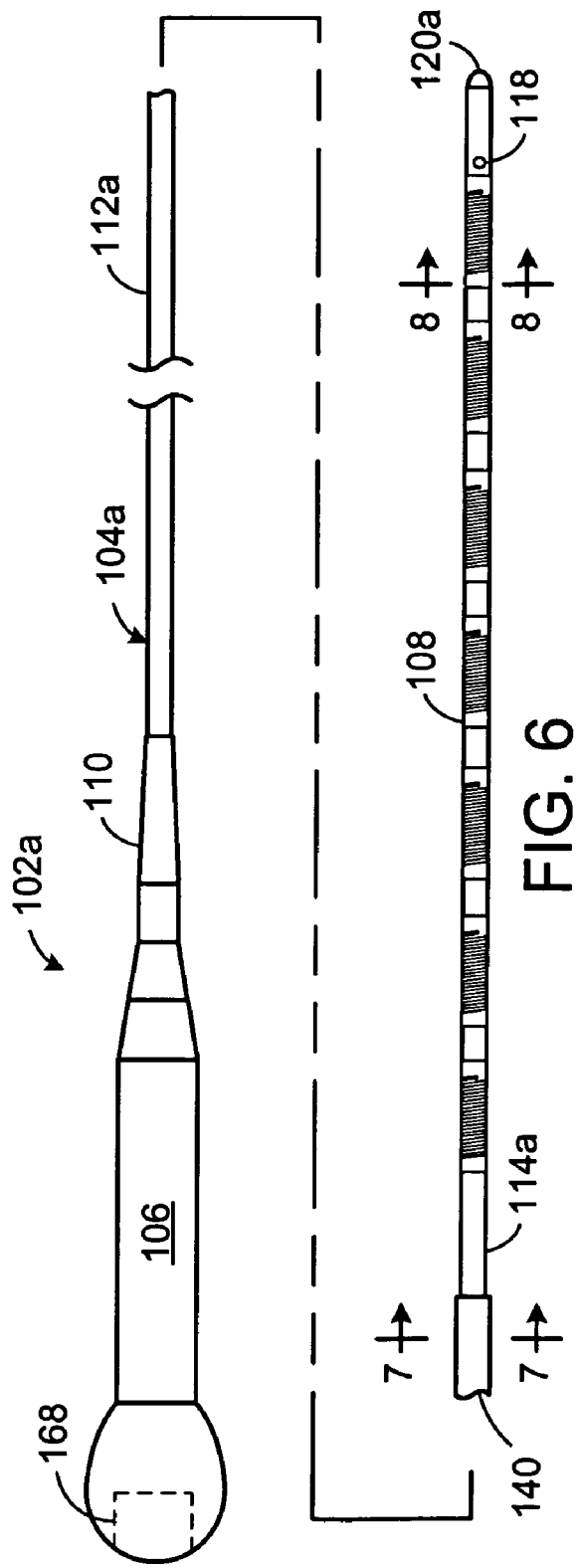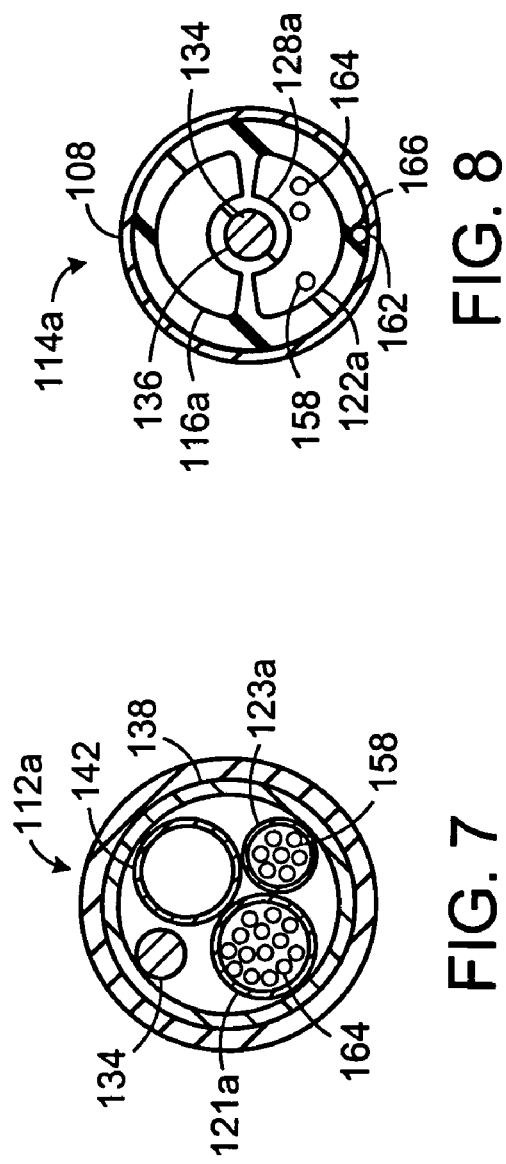
FIG. 6
FIG. 7
FIG. 8

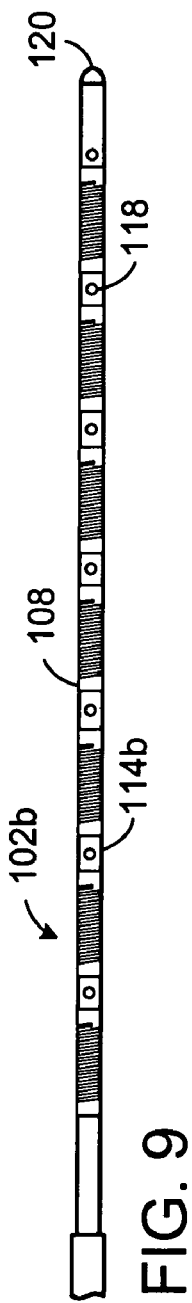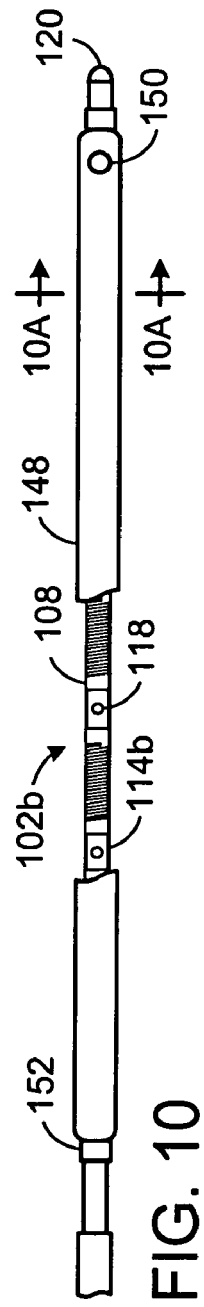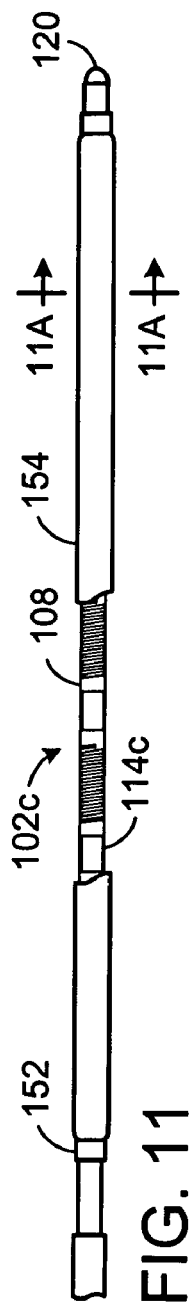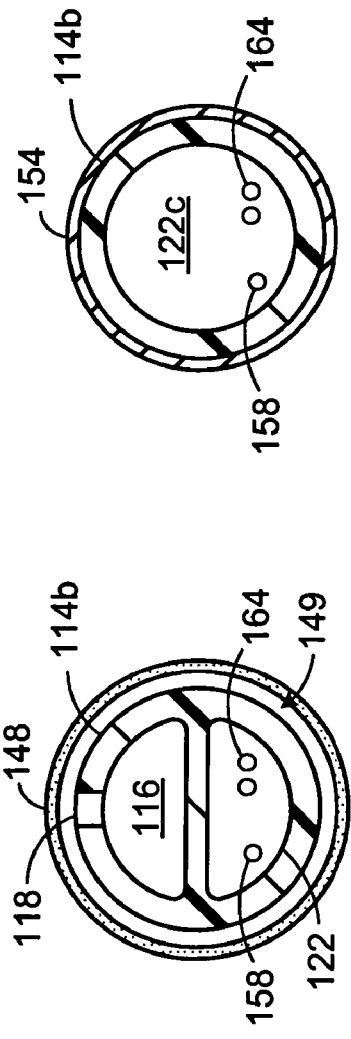

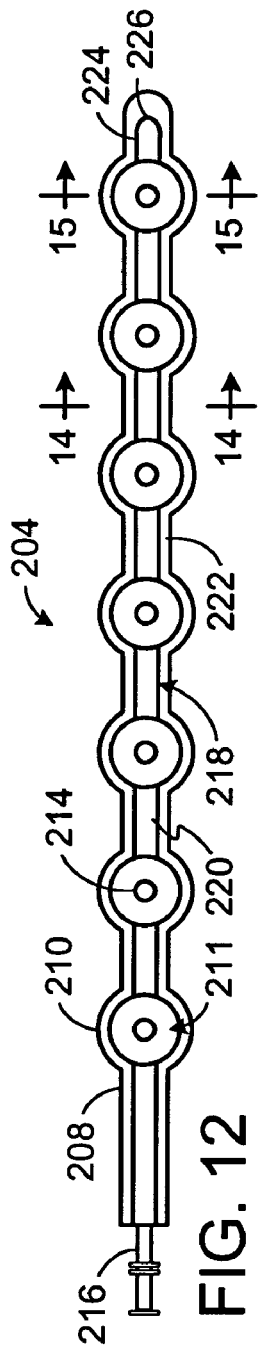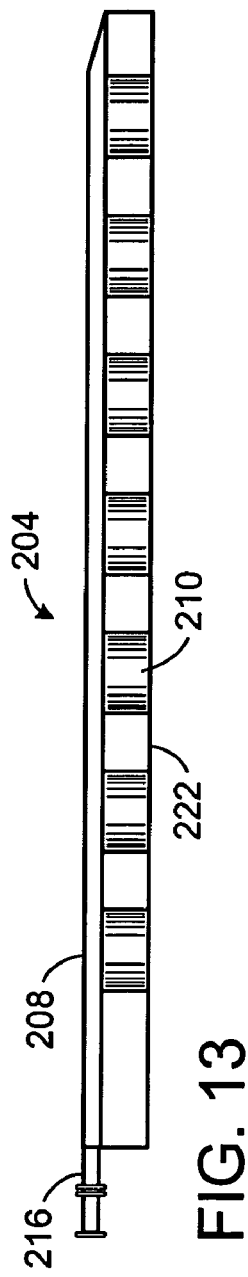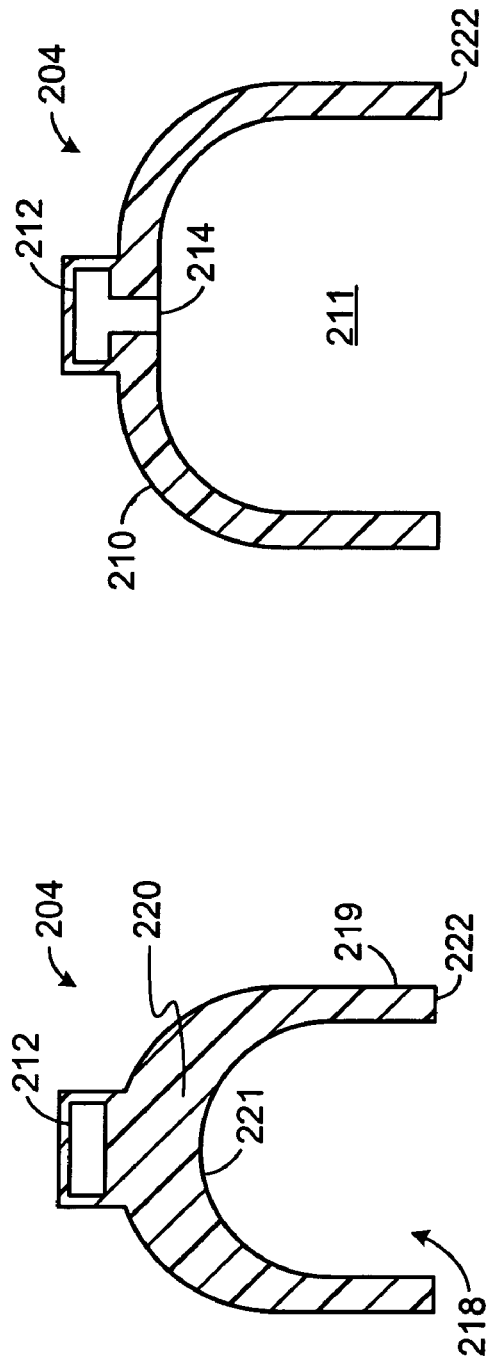

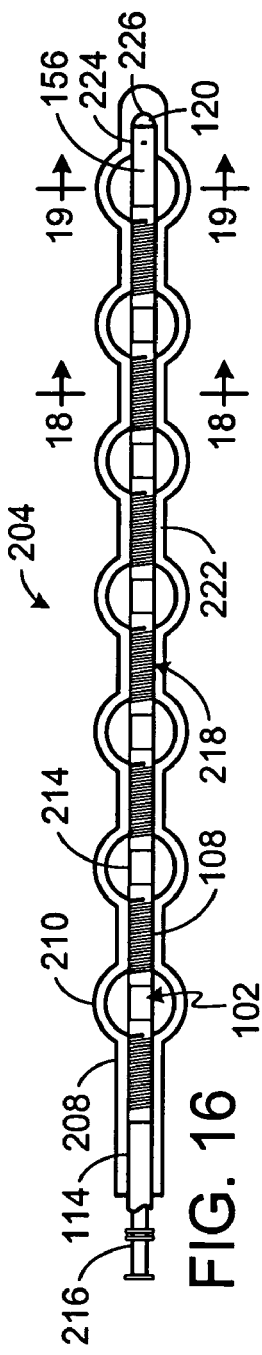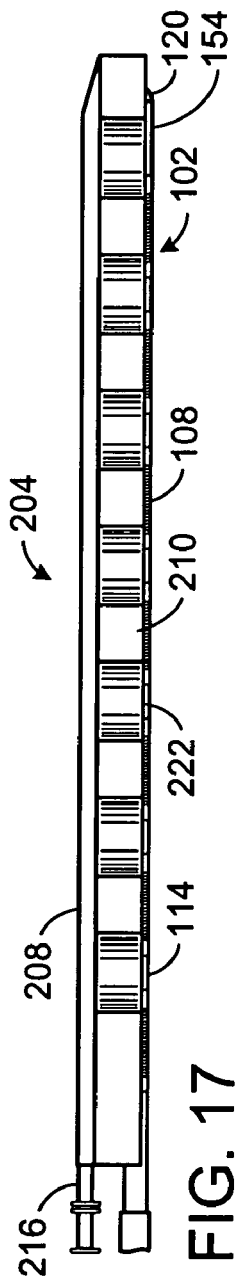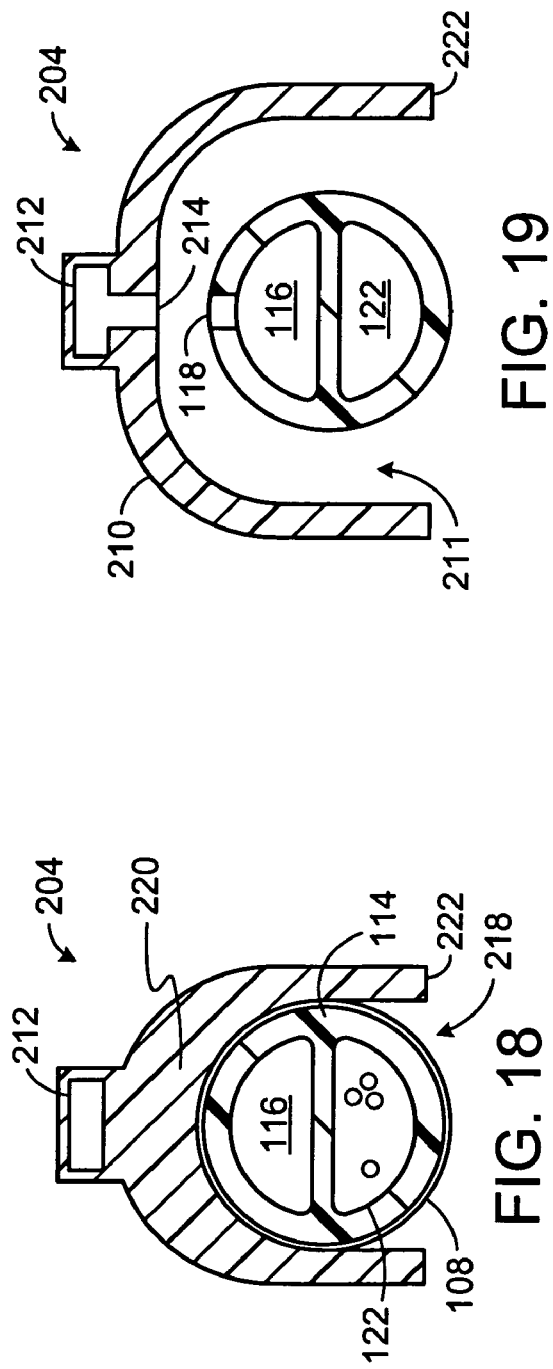

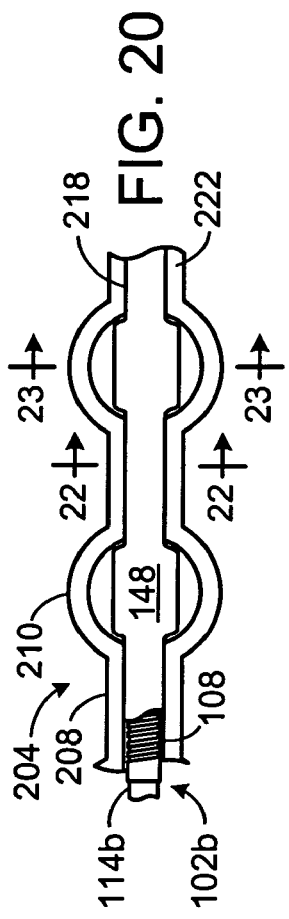
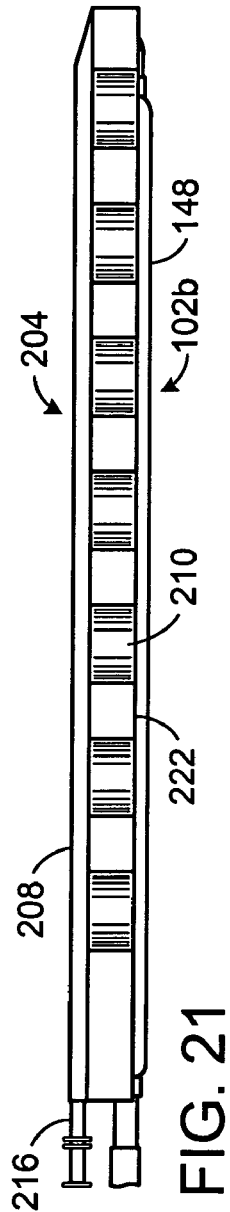
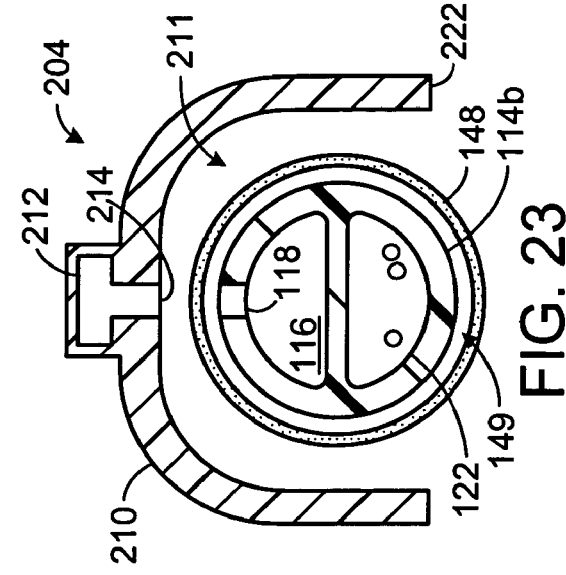
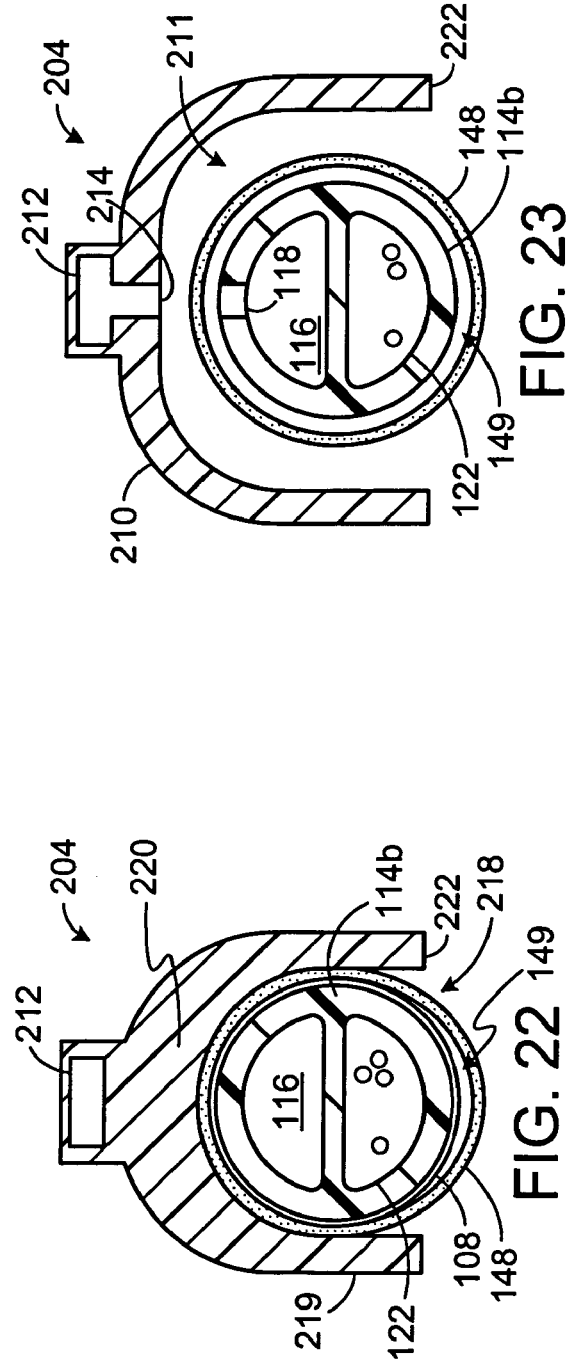

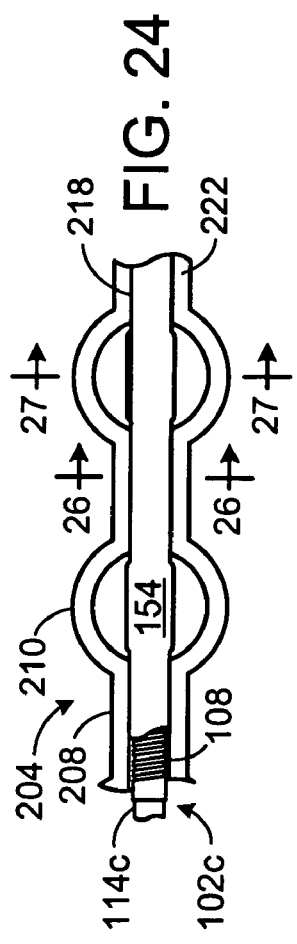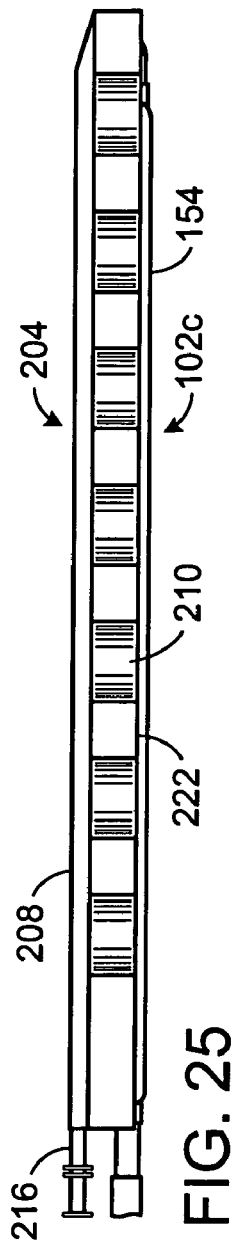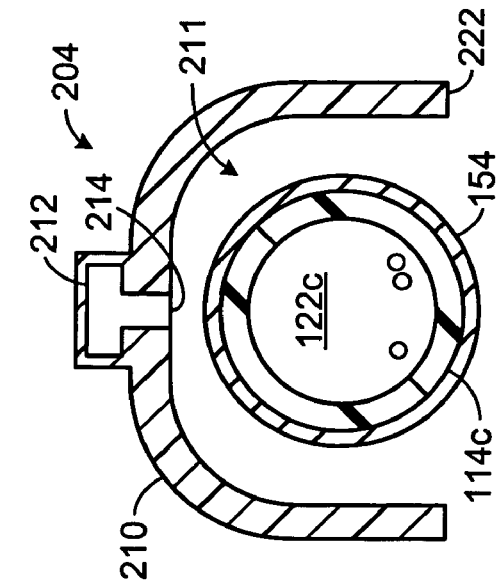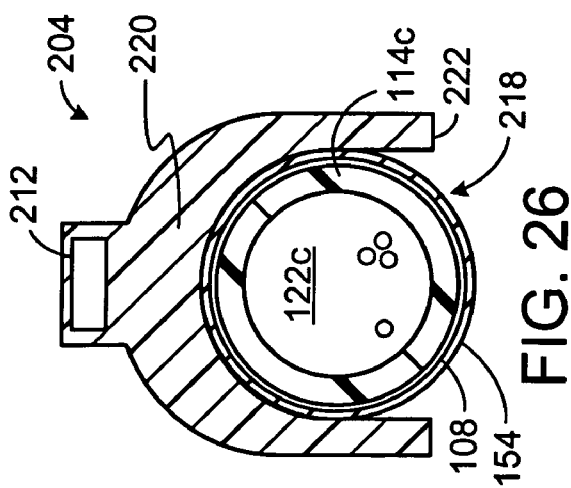

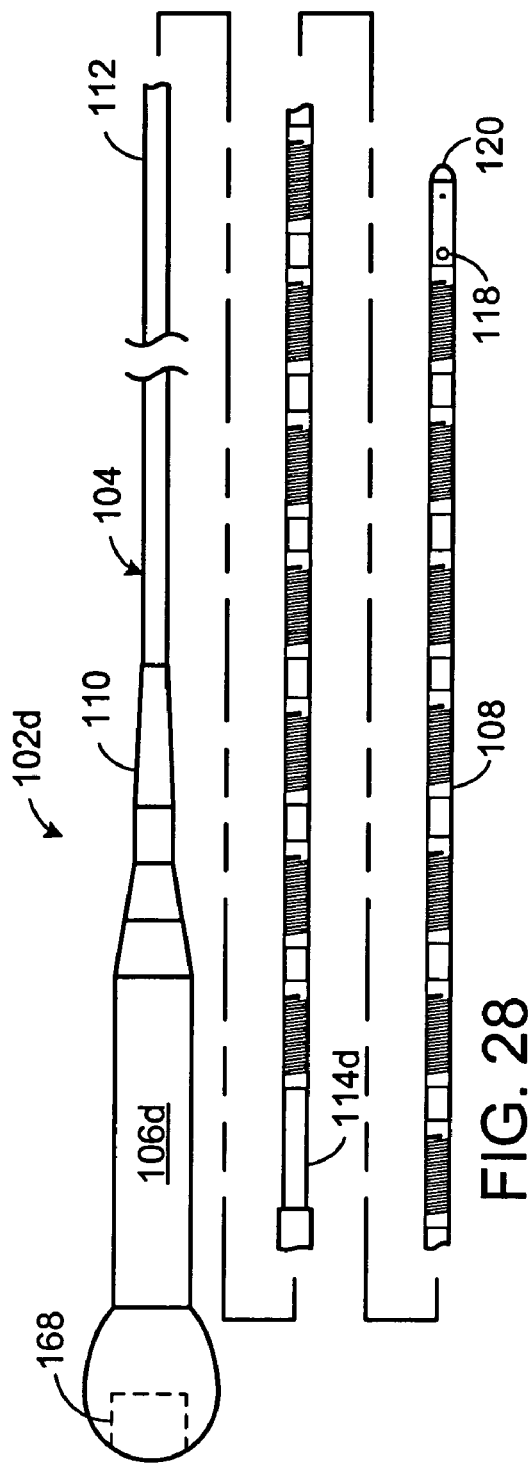
FIG. 28
FIG. 29
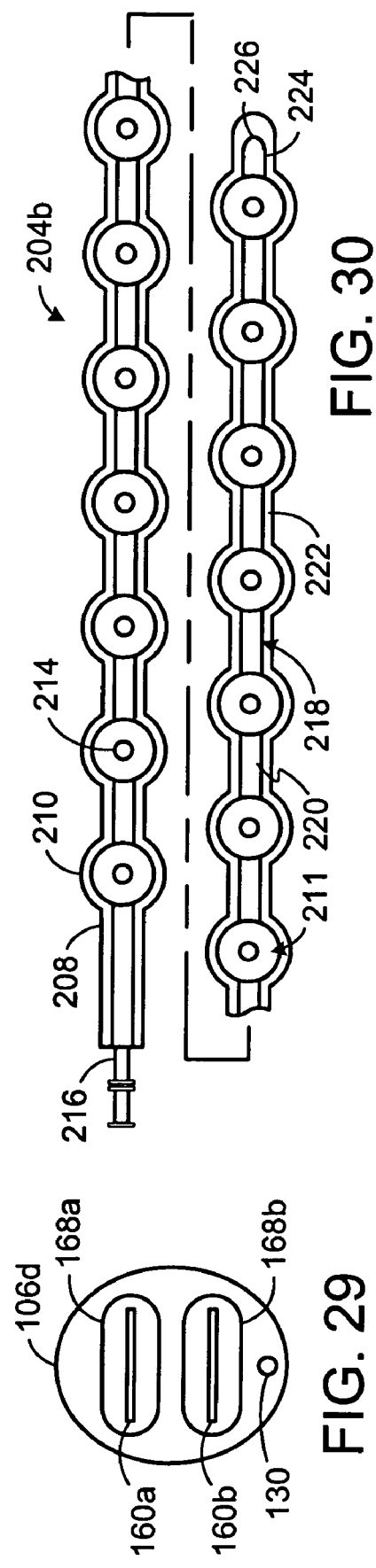
FIG. 30

COOLED PROBES AND APPARATUS FOR MAINTAINING CONTACT BETWEEN COOLED PROBES AND TISSUE

BACKGROUND OF THE INVENTIONS

1. Field of Inventions

The present inventions relate generally to devices for performing diagnostic and therapeutic operations on body tissue.

2. Description of the Related Art

There are many instances where diagnostic and therapeutic elements (referred to herein collectively as "operative elements") must be positioned adjacent to body tissue. One instance involves the formation of therapeutic lesions to the treat cardiac conditions such as atrial fibrillation, atrial flutter and arrhythmia. Therapeutic lesions may also be used to treat conditions in other regions of the body including, but not limited to, the prostate, liver, brain, gall bladder, uterus and other solid organs. Typically, the lesions are formed by ablating tissue with one or more electrodes. Electromagnetic radio frequency ("RF") energy applied by the electrode heats, and eventually kills (i.e. "ablates"), the tissue to form a lesion. During the ablation of soft tissue (i.e. tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue. Depending on the procedure, a variety of different electrophysiology devices may be used to position a plurality of electrodes at the target location.

In recent years, devices such as surgical soft tissue coagulation probes that carry one or more diagnostic or therapeutic elements have been developed. These probes may be used, for example, in endocardial and epicardial procedures where access to the heart is obtained by way of a thoracostomy, thoracotomy or median sternotomy. Such probes also allow endocardial lesions to be formed as a secondary procedure during a primary open heart surgical procedure such as mitral valve replacement, aortic valve replacement, and coronary artery bypass grafting. In either case, it is frequently desirable to create continuous linear lesions for therapeutic purposes.

Tissue contact can be an issue in any electrophysiology procedure, including those which involve the use of surgical probes for diagnostic and therapeutic purposes. The failure to achieve and maintain intimate contact between the tissue and operative elements can result in gaps in what were intended to be continuous linear lesions. Such gaps may result in a failure to cure the patient's arrhythmia and atrial flutter or may create atrial flutter. Moreover, atrial flutter created by gaps in linear lesions can difficult to cure. Poor contact between the tissue and operative elements can also result in lesions that are not transmural. Lesion which are not transmural may, in turn, fail to cure the patient's arrhythmia or other medical condition.

Another issue in electrophysiology procedures is operative element positioning and, more specifically, preventing the operative elements from moving after the physician has placed them adjacent to the target tissue region.

Tissue temperature can also be an issue in lesion creation procedures. For example, a relatively wide deep lesion may be created by reducing the temperature of the tissue closest to the electrode(s). This shifts the hottest iso-thermal region deeper into the tissue, thereby enabling higher power to be delivered without causing char or excessive surface desiccation to occur. Higher power, in turn, results in a larger volume of tissue being heated to a temperature sufficient to coagulate tissue (above 50° C.) and, therefore, a wider and deeper lesion.

SUMMARY OF THE INVENTIONS

A suction device in accordance with a present invention may be used, for example, in combination with an electrophysiology device that includes at least one operative element and a fluid outlet. The suction device includes at least one suction pod defining a suction region and can be secured to the electrophysiology device such that the fluid outlet is within the suction region.

A suction device in accordance with a present invention may be used, for example, in combination with an electrophysiology device that includes at least one operative element. The suction device includes at least one suction pod and can be secured to the electrophysiology device such that a portion of the electrophysiology device extends below the bottom surface of the suction pod.

A suction device in accordance with a present invention may be used, for example, in combination with an electrophysiology device that includes at least one operative element. The suction device includes at least two longitudinally spaced suction pods and can be secured to the electrophysiology device such that the substantial majority of the operative element is between the suction pods.

The present inventions also encompass suction systems including a suction device, electrophysiology systems including an electrophysiology device and a suction device, and methods involving the use of a suction device in combination with an electrophysiology device.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 2 is a plan view of a probe in accordance with a preferred embodiment of a present invention.

FIG. 3 is a section view taken along line 3-3 in FIG. 2.

FIG. 4 is a section view taken along line 44 in FIG. 2.

FIG. 5 is an end view of the probe illustrated in FIG. 2.

FIG. 6 is a plan view of a probe in accordance with a preferred embodiment of a present invention.

FIG. 7 is a section view taken along line 7-7 in FIG. 6.

FIG. 8 is a section view taken along line 8-8 in FIG. 6.

FIG. 9 is a plan view of a portion of a probe in accordance with a preferred embodiment of a present invention.

FIG. 10 is a plan view of a portion of a probe in accordance with a preferred embodiment of a present invention.

FIG. 10A is a section view taken along line 10A-10A in FIG. 10.

FIG. 11 is a plan view of a portion of a probe in accordance with a preferred embodiment of a present invention.

FIG. 11A is a section view taken along line 11A-11A in FIG. 11.

FIG. 12 is a bottom view of a suction device in accordance with a preferred embodiment of a present invention.

FIG. 13 is a side view of the suction device illustrated in FIG. 13.

FIG. 14 is a section view taken along line 14-14 in FIG. 12.

FIG. 15 is a section view taken along line 15-15 in FIG. 12.

FIG. 16 is a bottom view of showing a portion of the probe illustrated in FIGS. 2-5 secured to the suction device illustrated in FIGS. 12-15.

FIG. 17 is a side view of showing a portion of the probe illustrated in FIGS. 2-5 secured to the suction device illustrated in FIGS. 12-15.

FIG. 18 is a section view taken along line 18-18 in FIG. 16.

FIG. 19 is a section view taken along line 19-19 in FIG. 16.

FIG. 20 is a bottom view of showing a portion of the probe illustrated in FIGS. 10 and 10A secured to the suction device illustrated in FIGS. 12-15.

FIG. 21 is a side view of showing a portion of the probe illustrated in FIGS. 10 and 10A secured to the suction device illustrated in FIGS. 12-15.

FIG. 22 is a section view taken along line 22-22 in FIG. 20.

FIG. 23 is a section view taken along line 23-23 in FIG. 20.

FIG. 24 is a bottom view of showing a portion of the probe illustrated in FIGS. 11 and 11A secured to the suction device illustrated in FIGS. 12-15.

FIG. 25 is a side view of showing a portion of the probe illustrated in FIGS. 11 and 11A secured to the suction device illustrated in FIGS. 12-15.

FIG. 26 is a section view taken along line 26-26 in FIG. 24.

FIG. 27 is a section view taken along line 27-27 in FIG. 24.

FIG. 28 is a plan view of a probe in accordance with a preferred embodiment of a present invention.

FIG. 29 is an end view of the probe illustrated in FIG. 28.

FIG. 30 is a bottom view of a suction device in accordance with a preferred embodiment of a present invention.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Exemplary System Overview
II. Exemplary Surgical Probe Systems
III. Exemplary Fluid Retaining Structures
IV. Exemplary Suction System
V. Exemplary Operative Elements, Temperature Sensing And Power Control The section titles and overall organization of the present detailed description are for the purpose of convenience only and are not intended to limit the present inventions.

This specification discloses a number of structures, mainly in the context of cardiac treatment, because the structures are well suited for use with myocardial tissue. Nevertheless, it should be appreciated that the structures are applicable for use in therapies involving other types of soft tissue. For example, various aspects of the present inventions have applications in procedures concerning other regions of the body such as the prostate, liver, brain, gall bladder, uterus and other solid organs.

I. Exemplary System Overview

Figure 1:
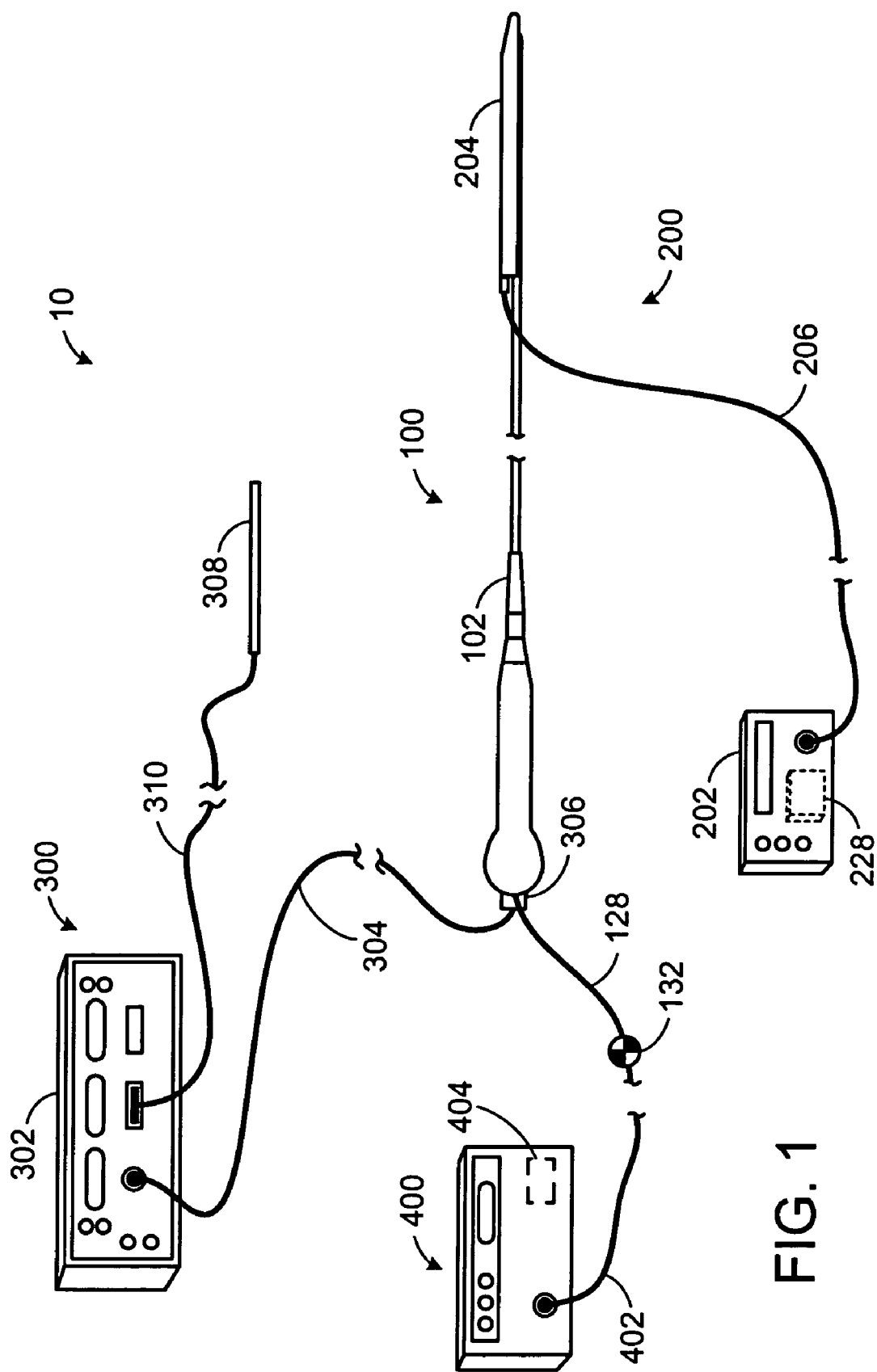
FIG. 1 is a perspective view of an electrophysiology system in accordance with a preferred embodiment of a present invention.

As illustrated for example in FIG. 1, an electrophysiology system 10 in accordance with a preferred embodiment of a present invention includes a surgical probe system 100 and a suction system 200. The exemplary surgical probe system 100 includes a surgical probe 102. The exemplary suction system 200 includes a suction source 202 and a suction device 204 that may be removably secured to the distal portion of the surgical probe 102. When the suction source 202 is actuated, the suction device 204 will fix the position of the distal portion of the surgical probe 102 relative to the target tissue. The applied vacuum will also insure that the tissue and operative elements carried by the surgical probe 102 make good contact with one another. A power supply and control system 300 may be provided to supply power to the surgical probe 102 and a cooling fluid supply device 400 may be used to supply cooling fluid that reduces the temperature of the tissue closest to the electrodes. In some implementations, the cooling fluid will travel through a fluid supply lumen within the probe to the electrode supporting distal portion.

There are a number of advantages associated with the exemplary electrophysiology system 10. For example, the suction device 204 may be used to convert a surgical probe such as the surgical probe 102, which does not have suction capabilities, into a surgical probe that does. The suction device 204 may also be used to convert other types of electrophysiology systems and devices, such as steerable and non-steerable diagnostic and/or therapeutic catheters, into a surgical probe with suction capabilities. Other advantages are associated with the use of cooling fluid to reduce the temperature of the tissue closest to the electrodes. Such cooling results in wider and deeper lesions than could otherwise be achieved without charring.

The exemplary suction system 200 may also be used to remove the cooling fluid from the patient. Use of the suction system 200 to remove the cooling fluid eliminates the need for a fluid return lumen within the probe and, because the perfusion length is reduced by half (as compared to a probe with the return lumen), the size of the cooling fluid supply lumen may be reduced. This facilitates the formation of lower profile probes that may be more readily positioned in open thoracic and minimally invasive procedures. Additionally, because the vacuum associated with the suction system 200 draws the cooling fluid out of the patient, the driving pressure required for the cooling fluid may be reduced.

II. Exemplary Surgical Probe Structure

The exemplary suction system 200, which is described in greater detail in Section IV below, may be used in combination with a wide variety of electrophysiology devices including, but not limited to, surgical probes, catheters, imaging devices, transducer arrays and diagnostic monitoring devices. Exemplary surgical probes and catheters are illustrated in U.S. Pat. Nos. 6,142,994 and 6,287,301.

As illustrated for example in FIGS. 2-5, the surgical probe 102 in the exemplary surgical probe system 100 includes a shaft 104, a handle 106, and a plurality of electrodes 108 or other operative elements on the shaft. A strain relief element 110 may also be provided. The exemplary shaft 104 includes a proximal portion 112 and a distal portion 114. The proximal portion 112, which is relatively long (e.g. about 30 cm to 100 cm for cardiac treatment applications) and flexible, is secured to the handle 106. This allows the proximal portion 112 to be conveniently draped over the patient and beyond after the distal portion 114 and electrodes 108 have been positioned at the target tissue location. The distal portion 114, which carries the electrodes 108, is relatively short (e.g. about 2 cm to 25 cm for cardiac treatment applications) and is also flexible. The shaft proximal and distal portions 112 and 114 may be a unitary structure or, alternatively, may be two separate structures that are secured to one another during assembly. The shaft proximal and distal portions 112 and 114 are also preferably formed from electrically non-conductive material.

The exemplary surgical probe system 100 is a cooled surgical probe system and, more specifically, the surgical probe system employs fluid to cool the electrodes 108 or other operative elements (and, accordingly, reduce the temperature of the adjacent tissue) during coagulation procedures. As described in greater detail below, heat from the electrodes 108 is transferred to the fluid to cool the electrodes while energy is transferred from the electrodes to the tissue. Cooling the electrodes 108 (and the adjacent tissue) during a coagulation procedure facilitates the formation of lesions that are wider and deeper than those that could be realized with an otherwise identical device which lacks the present cooling apparatus. Additionally, although gaseous cooling fluid may be employed, liquid is preferred.

Referring more specifically to FIGS. 2-4, the electrode cooling apparatus in the exemplary system 100 is composed primarily of the shaft distal portion 114 and a fluid inlet lumen 116, which is formed in the proximal portion 112 as well as the distal portion. Heat from the electrodes 108 is transferred through the distal portion 114 to fluid that is flowing through the inlet lumen 116. Accordingly, in addition to being electrically non-conductive, the material used to form the distal portion 114 should be relatively high in thermal conductivity. As used herein, "relatively high" thermal conductivity is at least about 1 W/m·K and preferably ranges from about 1 to about 10 W/m·K. The fluid exits the inlet lumen 116 through an outlet aperture 118 that is distal of the distal most electrode 108 in the exemplary embodiment. The fluid is removed from the patient by the suction system 200 in the manner described in Section IV below.

Suitable electrically non-conductive, thermally conductive thermoplastics for the distal portion 114 include flexible thermoplastic polymer materials, such as nylon or polyurethane, which are filled with a filler that promotes heat transfer. Suitable fillers include graphite, aluminum, tungsten and ceramic powders. Another suitable filler is Carborundum CarboTherm™ boron nitride powder manufactured by Saint-Gobain in Cavaillon, France. The proximal portion 112, on the other hand, does not have relatively high thermal conductivity and may be formed from, for example, flexible non-conductive thermoplastics such as Pebax® material and polyurethane.

A tip member 120 (FIG. 2) is secured to the shaft distal portion 114 with adhesive or other suitable instrumentalities. The tip member 120 is preferably an electrically non-conductive plastic device that includes a pair of plugs (not shown) to seal the inlet lumen 116 and a power and signal wire lumen 122. The power and signal wire lumen 122, as well as the power and signal wires 158 and 164 located therein, is discussed in greater detail in Section V below.

In the exemplary implementation illustrated in FIGS. 2-5, where the shaft proximal and distal portions 112 and 114 are separate structures, the proximal portion may be larger in diameter than the distal portion because the proximal portion will be for the most part outside the patient. This configuration allows the cross-sectional areas of the fluid inlet lumen 116 within the proximal portion 112 to be maximized, thereby minimizing fluid flow resistance. There will be a step-down in the cross-sectional areas of the inlet lumen 116 where the proximal portion 112 is secured to the distal portion 114 in such a configuration. In the exemplary implementation, the outer diameter of the proximal portion 112 will be about 3 mm to about 5 mm, while the outer diameter of the distal portion 114 will be about 1.66 mm to 3.3 mm.

The exemplary shaft proximal and distal portions 112 and 114 are multi-lumen structures, each of which includes the fluid inlet lumen 116 and the power and signal wire lumen 122. Alternatively, separate lumens may be provided for the power and signal wires 158 and 164. The power and signal wire lumen 122 may also be eliminated altogether in those instances where the power and signal wires 158 and 164 are sufficiently insulated and/or the cooling fluid is sufficiently non-conductive.

In addition to the aforementioned fillers, heat transfer may be promoted by minimizing the thickness of the electrically non-conductive material between the inlet lumen 116 and the electrodes 108 within the distal portion 114 and by maximizing the cross-sectional area of the inlet lumen within the distal and proximal portions of the shaft. With respect to the shaft distal portion 114 illustrated in FIG. 4, for example, in an implementation where the outer diameter of the distal portion is about 8 French (2.66 mm), the thickness of the outer wall 124 between the electrode 108 and the inlet lumen 116 will be about 0.08 mm to about 0.36 mm. It should be noted that when the outer wall thickness is about 0.02 mm or less, materials with less than "relatively high" thermal conductivities, such as Pebax® material and polyurethane, may also be used for the distal portion.

In order to allow the cooling fluid inlet lumen 116 to occupy as much of the cross-sectional area and circumferential area of the shaft 104 as possible, the power and signal wire lumen 122 should be just large enough to accommodate the power and signal wires 158 and 164. The width of the inlet lumen 116 (i.e. the distance between the outer wall 124 and the inner region 126) should be at least 2 times the thickness of outer wall and, preferably 4 times the thickness of the outer wall. In the implementation where the outer diameter of the distal portion 114 is about 8 French (2.66 mm), and the thickness of the outer wall 124 is about 0.10 mm to about 0.25 mm, the width of the inlet lumen 116 preferably about 0.51 mm to about 1.02 mm.

As illustrated for example in FIG. 1, fluid may be supplied to the surgical probe 102 by way of an infusion lumen 128, which is connected to the inlet lumen 116. The infusion lumen 128 extends through an aperture 130 in the handle 104 (FIG. 5). The proximal end of the infusion lumen 128 is provided with an on-off valve 132, which may be connected to an infusion line 402 associated with the cooling fluid supply device 400. The cooling fluid supply device 400 also includes a controller 404. An infusion pump capable of variable flow rates is one example of a suitable fluid supply device. The cooling fluid itself is not limited to any particular fluid. Preferably, however, the fluid will be a low or electrically non-conductive fluid such as sterile water or 0.9% saline solution in those instances where the fluid will not be used to transmit current to tissue.

With respect to fluid temperature and flow rate, a suitable inlet temperature is about 0 to 25° C. and the fluid supply device 400 may be provided with a suitable cooling system to bring the temperature of the fluid down to the desired level. Although the fluid temperature will rise as heat is transferred to the fluid, the temperature will remain low enough to draw heat from the electrodes 108 as it flows through the inlet lumen 116. In a seven electrode embodiment such as those illustrated in FIGS. 1-5 where 150 W is being supplied to the electrodes 108, for example, a suitable constant fluid flow rate is about 4 ml/min to about 20 ml/min. In an open system where heated fluid is not returned to the fluid supply device 400, such as that illustrated in FIG. 1, the fluid supply device should include enough fluid to complete the procedure. 60 ml would, for example, be required for a 3 minute procedure where the flow rate was 20 ml/min.

Another exemplary surgical probe is generally represented by reference numeral 102a in FIGS. 6-8. Surgical probe 102a is a fluid cooled surgical probe that is substantially similar to the surgical probe 102 illustrated in FIGS. 1-5 and similar elements are represented by similar reference numerals. Here, however, the proximal portion 112a of the shaft 104a is flexible and the distal portion 114a is malleable. As used herein, a "malleable" object is an object that can be readily bent by the physician to a desired shape, without springing back when released, so that it will remain in that shape during the surgical procedure. Thus, the stiffness of a malleable object must be low enough to allow the object to be bent, but high enough to resist bending when the forces associated with the intended electrophysiology procedure.

In the exemplary embodiment illustrated in FIGS. 6-8, the proximal portion 112a is formed primarily by a flexible outer tube, while the distal portion 114a includes a malleable wire 134 that allows the physician to bend the distal portion into the desired shape. The distal portion 114a is provided with a central lumen 136 to accommodate the malleable wire 134. One end of the malleable wire 134 is mounted in the tip member 120a and the other end is soldered or otherwise secured to a relatively short (e.g. about 2 cm) hypotube 138 that is positioned within the distal end 140 of the proximal portion 112a. The proximal portion 112a also houses fluid inlet tube 142, which is connected to the fluid inlet lumen 116a in the distal portion 114a and to the infusion lumen 128 in the handle 106, and power and signal wire tubes 121a and 123a, which are connected to the power and signal wire lumen 122a in the distal portion.

The distal portion 114b of another exemplary probe 102b, which is substantially identical to the probe 102 illustrated in FIGS. 2-5, is shown in FIG. 9. Here, however, there are fluid outlet apertures 118 adjacent to each of the electrodes 108 instead of only the distal most electrode. Cooling fluid exits the inlet lumen 116 through each of the outlet apertures 118. The multi-outlet lumen arrangement allows coagulation procedures to proceed in such a manner that vaporization of the cooling fluid is the primary source of electrode cooling. This may be accomplished by applying a relatively high vacuum pressure to the suction device 204. Generally speaking, reducing the atmospheric pressure within the suction device reduces the vapor pressure of the cooling fluid. Reducing the vapor pressure to a level which corresponds to a cooling fluid boiling point of about 60° C. facilitates vaporization of the cooling fluid during coagulation procedures. Additional details concerning this method of cooling are discussed in the context of the suction device 204 in Section IV below.

Additional details concerning cooled surgical probes with both flexible and malleable distal sections may be found in U.S. Patent Application Pub. No. 2003/0078644, which is incorporated herein by reference.

III. Exemplary Fluid Retaining Structures

The distal portion of probes in accordance with the present inventions may, in some instances, be covered with one or more fluid retaining structures. There are a variety of advantages associated with the use of the fluid retaining structures such as, for example, keeping the tissue moist and preventing desiccation.

As illustrated for example in FIGS. 10 and 10A, a nanoporous outer casing 148 is supported on the distal portion 114b of probe 102b. The outer casing 148, which receives ionic cooling fluid from the cooling fluid supply device 400 (FIG. 1) by way of the fluid inlet lumen 116 and outlet apertures 118, is secured to the probe distal portion 114b over the electrodes 108 such that a fluid space 149 is defined therebetween. The fluid space 149 will typically be about 0.2 mm high, measured from the outer surface of the electrodes 108 to the inner surface of the casing 148. The pores in the nanoporous outer casing 148 allow the transport of ions contained in the fluid through the casing and into contact with tissue. Thus, when an electrode 108 transmits RF energy into the ionic fluid, the ionic fluid establishes an electrically conductive path through the outer casing 148 to the tissue being coagulated.

The proximal and distal ends of the exemplary outer casing 148 are secured to the distal portion 114b with anchoring devices 152, such as lengths of heat shrink tubing, Nitinol tubing or other mechanical devices that form an interference fit between the casing and the base member. Adhesive bonding is another method of securing the outer casing 148 to the distal portion 114b.

Initially, the cooling fluid passing through the fluid inlet lumen 116 and outlet apertures 118 will fill the fluid space 149. Once the fluid space 149 is filled, cooling fluid will exit the fluid space through an outlet aperture 150 in the distal end of the outer casing 148 as additional cooling fluid enters to outer casing. This fluid is then removed from the patient by the suction system 200 in the manner described in Section IV below.

The electrically conductive ionic fluid preferably possesses a low resistivity to decrease ohmic loses, and thus ohmic heating effects, within the outer casing 148. The composition of the electrically conductive fluid can vary. In the illustrated embodiment, the fluid is a hypertonic saline solution, having a sodium chloride concentration at or near saturation, which is about 5% to about 25% weight by volume. Hypertonic saline solution has a relatively low resistivity of only about 5 ohm-cm, as compared to blood resistivity of about 150 ohm-cm and myocardial tissue resistivity of about 500 ohm-cm. Alternatively, the ionic fluid can be a hypertonic potassium chloride solution.

With respect to temperature and flow rate, a suitable inlet temperature for epicardial applications (the temperature will, of course, rise as heat is transferred to the fluid) is about 0 to 25° C. with a constant flow rate of about 2 to 10 ml/min.

The flow rate required for endocardial applications where blood is present would be about three-fold higher (i.e. 6 to 60 ml/min.). Should applications so require, a flow rate of up to 100 ml/min. may be employed. As noted above, in an open system such as that illustrated in FIG. 1 where heated fluid is not returned to the fluid supply device 400, the fluid supply device should include enough fluid to complete the procedure.

The fluid pressure within the outer casing 148 should be about 30 mm Hg in order to provide a structure that will resiliently conform to the tissue surface in response to a relatively small force normal to the tissue. Pressures above about 100 mm Hg will cause the outer casing 148 to become too stiff to properly conform to the tissue surface. For that reason, the flow resistance to and from the outer casing 148 should be relatively low.

Regenerated cellulose membrane materials, typically used for blood oxygenation, dialysis or ultrafiltration, are a suitable nanoporous material for the outer casing 148. The thickness of the material should be about 0.002 to 0.005 inch. Although regenerated cellulose is electrically non-conductive, the relatively small pores of this material allow effective ionic transport in response to the applied RF field. At the same time, the relatively small pores prevent transfer of macromolecules through the material, so that pressure driven liquid perfusion is less likely to accompany the ionic transport, unless relatively high pressure conditions develop within the outer casing 148.

Hydro-Fluoro™ material, which is disclosed in U.S. Pat. No. 6,395,325, is another material that may be used. Materials such as nylons (with a softening temperature above 100° C.), PTFE, PEI and PEEK that have nanopores created through the use of lasers, electrostatic discharge, ion beam bombardment or other processes may also be used. Such materials would preferably include a hydrophilic coating. Nanoporous to microporous materials may also be fabricated by weaving a material (such as nylon, polyester, polyethylene, polypropylene, fluorocarbon, fine diameter stainless steel, or other fiber) into a mesh having the desired pore size and porosity. These materials permit pressure driven transport of liquid (under relatively high pressure) as well as passage of ions in response to the applied RF field. Since these materials possess larger pore diameters, pressure driven liquid perfusion, and the attendant transport of macromolecules through the pores, are also more likely to occur. The fluid that is driven through the pores can be removed by the vacuum created by the suction device 204, primarily within the suction regions 211 (discussed below with reference to FIGS. 12-15), thereby obviating the need for the outlet aperture 150.

The electrical resistivity of the outer casing 148 will have a significant influence on lesion geometry and controllability. Low-resistivity (below about 500 ohm-cm) requires more RF power and results in deeper lesions, while high-resistivity (at or above about 500 ohm-cm) generates more uniform heating and improves controllability. Because of the additional heat generated by the increased resistivity within the outer casing 148, less RF power is required to reach similar surface tissue temperatures after the same interval of time. Consequently, lesions generated with high-resistivity structures usually have smaller depth. The electrical resistivity of the outer casing can be controlled by specifying the pore size of the material, the porosity of the material, and the water adsorption characteristics (hydrophilic versus hydrophobic) of the material. A detailed discussion of these characteristics is found in U.S. Pat. No. 5,961,513. A suitable electrical resistivity for epicardial and endocardial lesion formation is about 1 to 3000 ohm-cm measured wet.

Generally speaking, low or essentially no liquid perfusion through the nanoporous outer casing 148 is preferred. When undisturbed by attendant liquid perfusion, ionic transport creates a continuous virtual electrode at the tissue interface. The virtual electrode efficiently transfers RF energy without need for an electrically conductive metal surface.

Pore diameters smaller than about 0.1 μm retain macromolecules, but allow ionic transfer through the pores in response to the applied RF field. With smaller pore diameters, pressure driven liquid perfusion through the pores is less likely to accompany the ionic transport, unless relatively high pressure conditions develop within the outer casing 148. Larger pore diameters (up to 8 μm) can also be used to permit ionic current flow across the membrane in response to the applied RF field. With larger pore diameters, pressure driven fluid transport across the membrane is much higher and macromolecules (such as protein) and even small blood cells (such as platelets) could cross the membrane and contaminate the inside of the probe. Red blood cells would normally not cross the membrane barrier, even if fluid perfusion across the membrane stops. On balance, a pore diameter of 1 to 5 μm is suitable for epicardial and endocardial lesion formation. Where a larger pore diameter is employed, thereby resulting in significant fluid transfer through the porous region, a saline solution having a sodium chloride concentration of about 0.9% weight by volume would be preferred.

With respect to porosity, which represents the volumetric percentage of the outer casing 148 that is composed of pores and not occupied by the casing material, the magnitude of the porosity affects electrical resistance. Low-porosity materials have high electrical resistivity, whereas high-porosity materials have low electrical resistivity. The porosity of the outer casing 148 should be at least 1% for epicardial and endocardial applications employing a 1 to 5 μm pore diameter.

Turning to water absorption characteristics, hydrophilic materials are generally preferable because they possess a greater capacity to provide ionic transfer of RF energy without significant liquid flow through the material.

Wettable fluid retention elements are another type of fluid retaining element that may be used in conjunction with probes that do not include fluid lumens. The wettable fluid retention elements, which cool tissue (primarily by vaporization) and prevent desiccation, are simply saturated with ionic fluid such as saline prior to use. As illustrated for example in FIGS. 11 and 11A, an exemplary probe 102c includes a distal member 114c with a power and signal wire lumen 122c and without a fluid lumen. A wettable fluid retention element 154 is carried by the distal member 114c and positioned around the electrodes 108. Anchoring devices 152 hold the wettable fluid retention element 154 in place.

Suitable materials for the fluid retention element 154 include biocompatible fabrics commonly used for vascular patches (such as woven Dacron®), open cell foam materials, hydrogels, nanoporous, microporous and porous balloon materials (with very slow fluid delivery to the surface), and hydrophilic nanoporous or microporous materials. The effective electrical resistivity of the fluid retention element 154 when wetted with 0.9% saline (normal saline) should range from about 1 Ω-cm to about 2000 Ω-cm. A preferred resistivity for epicardial and endocardial procedures is about 1000 Ω-cm.

It should be noted that fluid retention elements may also be used in conjunction with probes, such as the exemplary probe 102b illustrated in FIG. 9, that have a fluid inlet line 116 and a plurality of outlet apertures 118. Supplying additional fluid to the wettable element 154 would be useful during coagulation procedures that are relatively long in duration and could result in all of the saline solution present at the beginning of the procedure being evaporated or otherwise consumed prior to the end of the procedure.

IV. Exemplary Suction System

As illustrated for example in FIG. 1, and as noted above, the exemplary suction system 200 includes a suction source 202 and a suction device 204. The suction source 202 may be any suitable device that is capable of supplying the desired partial vacuum, which will typically range from about 100 mmHg to about 600 mmHg. The suction device 204, which is connected to the suction source 202 with a flexible suction tube 206, may be removably secured to the distal portion 114 of the surgical probe 102 (or to all or part of another electrophysiology device, such as the distal portion of the surgical probe 102a). When the suction source 202 is actuated, the suction device 204 will affix itself to a tissue surface and hold the distal portion 114 of the surgical probe 102 in place relative to the tissue surface.

Turning to FIGS. 12-15, the exemplary suction device 204 includes a main body 208 and a plurality of individual suction pods 210. Each suction pod 210 defines a suction region 211. A suction line 212 extends through the main body 208 and is connected to each of the suction pods 210 by suction apertures 214. The suction tube 206 may be connected to the internal suction line 212 by a connector 216 such as, for example, the illustrated Luer connector. The suction device 204 also includes a connector that enables it to be removably secured to the surgical probe distal portion 114 (or 114a or part of other electrophysiology devices) such that a portion of the probe is at least partially within a suction region 211. Although the present inventions are not limited to any particular connector, the connector in the exemplary embodiment is a slot 218 into which the surgical probe distal portion 114 may be inserted. The slot 218 is defined by the portions of the main body 208 that are located proximal of the proximal-most suction pod 210, between the suction pods, and distal of the distal-most suction pod.

The exemplary slot 218 is generally U-shaped in cross-section. The distance between the linear portions 219, as well as the diameter of the semi-circular portion 221, will preferably be slightly less than the diameter of the surgical probe distal portion 114. As such, the probe distal portion 114 may be removably pressed into the slot 218 to create an air-tight interference fit therebetween. Additionally, the main body includes suction pod separators 220 that define the top, semi-circular portion 221 of the slot 218. The separators 220 form an air-tight seal in the area between the suction pods 210 when the distal portion 114 (and electrodes 108) are pressed against the semi-circular portion 221, thereby isolating the suction pods 210 from one another.

Another exemplary connector that may be employed is a slot that is generally C-shaped in cross-section. Such a connector would form a snap-fit connection with the associated probe.

Figure 15A:
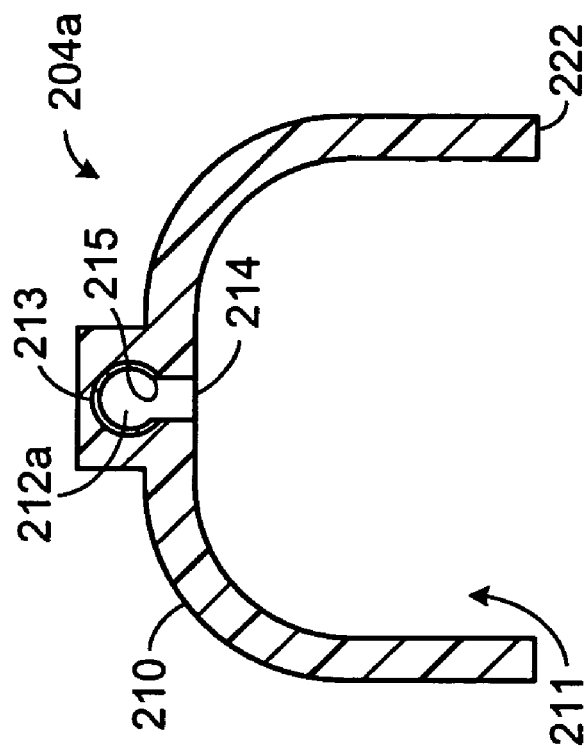
FIGS. 14A and 15A are section views of a suction device in accordance with a preferred embodiment of a present invention.
Figure 15B:
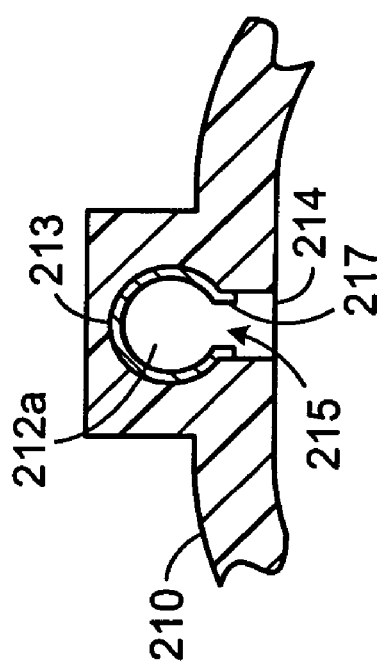
FIG. 15B is a section view of a suction device in accordance with a preferred embodiment of a present invention.
Figure 14A:
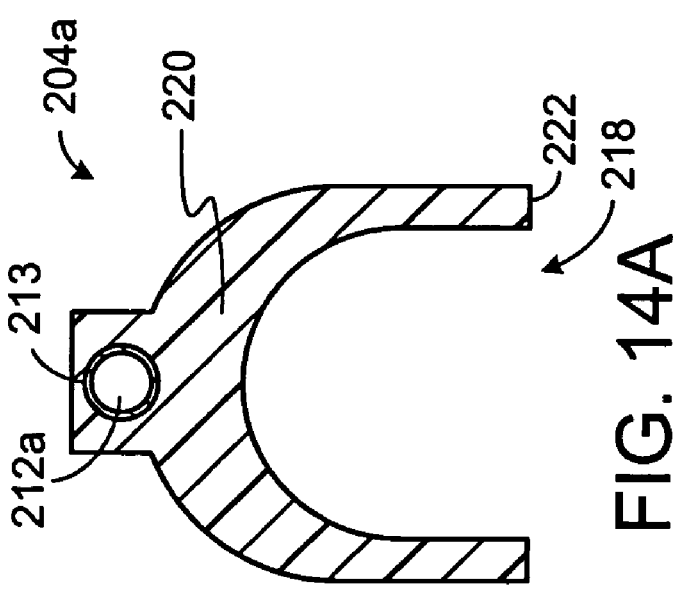

Suction devices in accordance with the present inventions may also be malleable. As illustrated in FIGS. 14A and 15A, the suction line 212a in the exemplary suction device 204a, which is otherwise identical to the suction device 204, is formed by a malleable hypotube 213. The malleable hypotube 213 is connected to the connector 216, and includes apertures 215 that are aligned with the suction apertures 214. Preferably, such a suction device will be formed by an insert molding process. In order to prevent the hypotube apertures 215 from moving out of alignment with the suction apertures 214 during use, the malleable hypotube 213 may be provided with cylindrical extensions 217, as illustrated for example in FIG. 15B. The extensions 217 are aligned with the hypotube apertures 215 and extend into the suction apertures 214. The descriptions above and below concerning the use of suction device 204 are also applicable to the suction device 204a.

When the exemplary suction device 204 is connected to the distal portion 114 of the probe 102 by inserting the distal portion into the slot 218 in the manner illustrated in FIGS. 16-19, the bottom of the probe distal portion and electrodes 108 will extend a short distance (e.g. about 0.5 mm) beyond the bottom surface 222 of the suction device. During use, the probe/suction device assembly will be pressed against tissue until the bottom surface 222 comes in contact with the tissue. The bottom surface 222 will form a seal with the tissue surface and air within the suction pods 210 will be drawn through the apertures 214 when the suction force is applied, thereby causing the suction device 204 to adhere to the tissue surface. Additionally, and depending on the rigidity of the suction device 204 and the rigidity of the tissue, portions of the suction device will deflect, portions of the tissue surface will deflect, or portions of both the suction device and the tissue surface will deflect.

It should also be noted that the probes and suction devices may be respectively configured in the exemplary implantation such that the size and spacing of the electrodes 108 corresponds to the size and spacing of the suction pods 210. For example, the probe 102 and suction device 204 are also respectively configured such that the gaps between the electrodes 108 will be aligned with the center of the suction pods 210 when the distal portion 114 is secured to the suction device in the manner illustrated in FIGS. 16-19. More specifically, the distal portion 224 of the slot 218 and the distal end 156 of the probe 102 are configured such that, when tip member 120 is against the distal end 226 of the slot 218, gaps between the electrodes 108 will be aligned with the center of the suction pods 210, and the electrodes will be aligned with the portions of the slot between the suction pods. This configuration also results in each of the outlet apertures 118 in the embodiment illustrated in FIG. 9 being located within a respective suction pod 210.

As illustrated for example in FIGS. 20-23, the exemplary suction device 204 may also be connected to the distal portion 114b of the probe 102b by inserting the distal portion into the slot 218 to create the interference fit. The portions of the outer casing 148 which are adjacent to the slot linear portions 219 and semicircular portion 221 will be pressed against the electrodes 108, while the bottom portion of the fluid space 149 will remain between the electrodes and outer casing in the areas between the suction pods 210 and proximal of the proximal-most suction pod. The portions of the outer casing 148 within the suction pods 210 will maintain its shape so that the fluid space 149 extends all the way around the probe distal portion 114b in those areas. As such, ionic cooling fluid exiting the inlet lumen 116 through an outlet apertures 118 will fill the fluid space 149, including the portions to the fluid space between the suction pods 210.

Turning to FIGS. 24-27, the exemplary suction device 204 may also be connected to the distal portion 114c of the probe 102c by inserting the distal portion into the slot 218 to create the interference fit. This will typically be done after the distal portion 114c, with the wettable fluid retention element 154, has been dipped in ionic fluid. The portions of the wettable fluid retention element 154 between the suction pods 210 may deform slightly, as shown in FIG. 24.

In addition to securing the distal portion of the probes to a tissue surface, the suction system 200 is also used to draw the cooling fluid out of the patient after it has passed through the probe. Referring first to FIGS. 1, 2 and 16-19, fluid exiting the inlet lumen 116 in probes 102 and 102*a* by way of the outlet aperture 118 will be drawn into the suction device 204 through the suction aperture 214 in the distal most suction pod 210. The fluid will then be drawn through the suction line 212 and the suction tube 206 on its way to the suction device 202. To that end, the suction device 202 in the exemplary embodiment is provided with a fluid receptacle 228 (FIG. 1) which collects the cooling fluid.

As noted above with reference to FIG. 9, the exemplary probe 102*b* includes a distal portion 114*b* with a plurality of outlet apertures 118 and the probe 102*b* and suction device 204 are configured such that each outlet aperture will be located within a respective suction pod 210. This arrangement allows coagulation procedures to proceed in such a manner that vaporization of the cooling fluid is the primary source of electrode cooling. This may be accomplished by applying a relatively high vacuum pressure to the suction device 204 generally. More specifically, in order to reduce the boiling point of the cooling fluid to the approximately 60° C. coagulation temperature, the absolute pressure within the suction pods 210 should be reduced to about 175 mm Hg. At sea level, an applied vacuum pressure of about −600 mm Hg will achieve 175 mm Hg within the suction pods 210. The vapor, which will be drawn into the suction device 202 by way of the suction line 212 and suction tube 206, will condense in the fluid receptacle 228 because it will be below the boiling temperature.

Turning to the exemplary probe 102*b* FIGS. 10, 10A and 20-23, cooling fluid will exit the probe by way of outlet aperture 150 in the distal end of the outer casing 148 after it has passed through the inlet lumen 116, outlet apertures 118 and outer casing. The cooling fluid will then be drawn through the into the suction device 204 through the suction aperture 214 in the distal most suction pod 210. Little to no perfusion through the outer casing 148 (other than the aperture 150) is anticipated. The cooling fluid will then be drawn into the suction device 202 and stored in the fluid receptacle 228 in the manner described above.

In those instances where a wettable fluid retention element such as the wettable fluid retention element 154 illustrated in FIGS. 11, 11A and 24-27 is employed, the conductive fluid stored by the wettable fluid retention element will vaporize during the coagulation procedure, thereby cooling the electrodes in the manner described above. Accordingly, the wettable fluid retention element 154 should store a volume of fluid sufficient to last for the entire coagulation procedure (e.g. about 45 seconds).

The specific size and shape of the suction device 204 will, of course, depend on the intended application, as will the choice of materials. Although the present inventions are not limited to any particular sizes, shapes or materials, one exemplary implementation that is especially well suited for cardiac treatment and use with the above-described surgical probes 102 and 102*a* is described hereafter. The suction device 204 is formed, preferably by molding, from a soft, flexible biocompatible material such as silicone rubber or urethane that is capable of withstanding temperatures up to 120° C. without melting or burning. When molded, the suction device 204 will be an integrally formed (i.e. one piece) structure, although some or all of the connector 216 may be added after molding depending on the type of connector employed. The overall length of the suction device 204, not including the connector 216, will be slightly longer than the shaft distal portion 114 (or 114*a*-114*c*), e.g. about 10 cm in an exemplary implementation where the distal portion is about 9 cm. The exemplary suction ports 210 are generally circular in shape when viewed from the bottom (FIG. 12) and have a diameter of about 11 mm and a depth of about 5 mm (FIG. 15). The distance between the top of the slot 218 and the bottom surface 222 is about 2.5 mm (FIG. 14). The suction apertures 214 are about 0.5 mm in diameter.

V. Electrodes, Temperature Sensing And Power Control

In each of the illustrated embodiments, a plurality of spaced electrodes adapted to transmit RF energy are employed. However, operative elements such as lumens for chemical ablation, laser arrays, ultrasonic transducers, microwave electrodes, ohmically heated hot wires, single elongate flexible electrodes and the like may be substituted for the spaced electrodes.

Although the present inventions are not limited to any particular number, the exemplary probes 102-102*c* each include seven spaced electrodes 108. The spaced electrodes 108 are preferably in the form of wound, spiral closed coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. Preferred coil electrodes are disclosed in U.S. Pat. Nos. 5,797,905 and 6,245,068.

Alternatively, the electrodes 108 may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel, silver or titanium can be applied. The electrodes can also be in the form of helical ribbons. The electrodes can also be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks. Open coil electrodes may also be employed.

The exemplary flexible electrodes 108 are preferably about 4 mm to about 20 mm in length. In the preferred embodiments, the electrodes are 12.5 mm in length with 1 mm to 3 mm spacing, which will result in an energy transmission region that is about 1 cm to about 14 cm in length and the creation of continuous lesion patterns in tissue when coagulation energy is applied simultaneously to adjacent electrodes. For rigid electrodes, the length of the each electrode can vary from about 2 mm to about 10 mm. Using multiple rigid electrodes longer than about 10 mm each adversely effects the overall flexibility of the device, while electrodes having lengths of less than about 2 mm do not consistently form the desired continuous lesion patterns.

With respect to operation, the exemplary electrodes 108 may be operated in a uni-polar mode, in which the soft tissue coagulation energy emitted by the electrodes is returned through an indifferent patch electrode (not shown) externally attached to the skin of the patient. Alternatively, the electrodes may be operated in a bi-polar mode, in which energy emitted by one or more electrodes is returned through other electrodes. Still another alternative is to supply power in the combined bi-polar/uni-polar mode described in U.S. application Ser. No. 10/368,108, which is entitled "Power Supply And Control Apparatus And Electrophysiology Systems For Use With Same." The amount of power required to coagulate tissue ranges from 5 to 150 w and depends on parameters such as set temperature and the flow rate of the fluid.

As illustrated for example in FIGS. 2-8, 10A and 11A, the electrodes 108 in the exemplary probes 102-102c are electrically coupled to individual power wires 158 that conduct coagulating energy to them. The power wires 158 are passed in conventional fashion through the associated lumen or tube to a PC board 160 within the handle 106. Preferably, a plurality of temperature sensors 162 such as thermocouples or thermistors, may be located on, under, abutting the longitudinal end edges of, or in between, the electrodes 108. A reference thermocouple (not shown) may also be provided. In the exemplary implementation, temperature sensors 162 are located at both longitudinal ends of each electrode 108. The temperature sensors 162 are connected to the PC board 160 by signal wires 164 that pass though the associated lumen or tube.

In the exemplary embodiment, the temperature sensors 154 are preferably located within a linear channel 166 (FIGS. 4 and 8) that is formed in the shaft distal portions 114-114c. The linear channel 166 insures that the temperature sensors will all face in the same direction (e.g. facing tissue) and be arranged in linear fashion. This arrangement results in more accurate temperature readings which, in turn, results in better temperature control. As such, the actual tissue temperature will more accurately correspond to the temperature set by the physician on the power supply and control device, thereby providing the physician with better control of the lesion creation process and reducing the likelihood that embolic materials will be formed. Such a channel may be employed in conjunction with any of the electrode support structures disclosed herein.

The power supply and control system 300 in the exemplary implementation illustrated in FIG. 1 includes an electrosurgical unit ("ESU") 302 that supplies and controls power, such RF power. A suitable ESU is the Model 4810A ESU sold by Boston Scientific Corporation of Natick, Mass. The ESU 302 transmits energy to the electrodes 108 and receives signal from the temperature sensors 162 by way of a cable 304 and a connector 306 arrangement. The connector 306 is configured to be inserted into a slot 168 (FIG. 5) on the surgical probe handle 106 and to mate with the PC board 160.

The exemplary ESU 302 illustrated is operable in a bipolar mode, where tissue coagulation energy emitted by one of the electrodes 108 is returned through one of the other electrodes, and a unipolar mode, where the tissue coagulation energy emitted by the electrodes 108 is returned through one or more indifferent electrodes 308 that are externally attached to the skin of the patient with a patch, or one or more electrodes (not shown) that are positioned in the blood pool, and a cable 310. The exemplary ESU 302 is also configured to individually power and control each electrode 108. Suitable temperature sensors and RF power supply and control devices are disclosed in U.S. Pat. Nos. 5,456,682, 5,582,609 and 5,755,715.

Although the present inventions have been described in terms of the preferred embodiments above, numerous modifications and/or additions to the above-described preferred embodiments would be readily apparent to one skilled in the art.

By way of example, but not limitation, the exemplary surgical probe 102d illustrated in FIGS. 28 and 29 is substantially similar to the surgical probe 102 illustrated in FIGS. 1-5 and similar elements are represented by similar reference numerals. Here, however, the distal portion 114d is twice as long and carries fourteen of the electrodes 108 instead of seven. Thus, the surgical probe 102d may be used to form longer continuous lesions than the surgical probe 102. One exemplary application of probes with a longer distal portion is the formation of lesions around pulmonary veins (either individually, one pair at a time, or all four at a time). In order to be used in combination with the exemplary ESU 302, which is not capable of individually controlling fourteen electrodes, the power wires and temperature sensor signal wires from the first set of seven electrodes 108 are connected to a first PC board 160a within the handle 106d, and the power and signal wires from the second set of seven electrodes are connected to a second PC board 160b. A pair of slots 168a and 168b allow the ESU connector 306 to be connected to the PC boards 160a and 160b. Turning to FIG. 30, the exemplary suction device 204b is substantially similar to the suction device 204 illustrated in FIGS. 12-15 and similar elements are represented by similar reference numerals. Here, however, the suction device is configured for use with the surgical probe 102d illustrated in FIGS. 28 and 29 and includes fourteen individual suction pods 210.

During a lesion formation procedure that involves some or all of the electrodes 108 in the both the first and second sets of seven electrodes, the ESU connector 306 may be connected to the PC boards 160a and 160b one at a time. For example, the connector 306 may be initially connected to the PC board 160a. After the distal portion 114d has been positioned, the suction force has been applied to the suction device 204b, and the flow of cooling fluid initiated, some or all of the electrodes 108 in the first set of seven may be used to form a lesion. Next, and in many instances without moving the distal portion 114d or discontinuing the application of suction force, the connector 306 may be connected to the PC board 160b so that lesions can be formed with some or all of the electrodes 108 in the second set of seven.

It is intended that the scope of the present inventions extend to all such modifications and/or additions and that the scope of the present inventions is limited solely by the claims set forth below. Additionally, the scope of the inventions includes any combination of the elements from the various species and embodiments disclosed in the specification that are not already described.

We claim:

1. A suction device for use with an electrophysiology device, the electrophysiology device including a shaft carrying an operative element and defining an internal fluid lumen and a fluid outlet, the suction device comprising:

a main body, a suction line extending through the main body;

at least one suction pod, a suction region being defined within the at least one suction pod and being connected to the suction line through a suction aperture formed through the at least one suction pod; and a connector configured to removably secure the shaft of the electrophysiology device to the suction device such that the shaft extends through the suction region and the fluid outlet defined by the shaft is within the suction region.

2. A suction device as claimed in claim 1, wherein the at least one suction pod comprises a plurality of suction pods, a suction region being defined within each suction pod and being connected to the suction line through a suction aperture, the shaft extending through a plurality of suction regions.

3. A suction device as claimed in claim 1, the suction line being configured to be connected to a suction source.

4. A suction device as claimed in claim 1, wherein the at least one suction pod comprises a flexible suction pod.

5. A suction device as claimed in claim 1, wherein the connector comprises a slot.

6. A suction device as claimed in claim 1, wherein the at least one suction pod comprises a plurality of suction pods, each suction pod defining a respective suction region connected to the suction line through a suction aperture, and the connector is configured to removably secure the shaft of an electrophysiology device to the suction device such that the shaft extends through a plurality of suction regions with each of a plurality of fluid outlets defined by the shaft located within a respective suction region.

7. A suction device for use with an electrophysiology device, the electrophysiology device including a shaft carrying an operative element, the suction device comprising:
a main body, a suction line extending through the main body;
at least one suction pod defining a bottom surface, at least one suction region being defined within the at least one suction pod and being connected to the suction line through a suction aperture formed through the at least one suction pod; and
a connector configured to removably secure the shaft of the electrophysiology device to the suction device such that a portion of the shaft extends through the at least one suction region and below the bottom surface of the suction pod.

8. A suction device as claimed in claim 7, wherein the at least one suction pod comprises a plurality of suction pods, a suction region being defined within each suction pod and being connected to the suction line through a suction aperture, the shaft extending through a plurality of suction regions.

9. A suction device as claimed in claim 7, the suction line being configured to be connected to a suction source.

10. A suction device as claimed in claim 7, wherein the at least one suction pod comprises a flexible suction pod.

11. A suction device as claimed in claim 7, wherein the connector comprises a slot.

12. A suction device as claimed in claim 7, wherein the connector is configured to removably secure the shaft to the suction device such that the portion of the shaft extends about 0.5 mm below the bottom surface of the suction pod.

13. A suction device for use with an electrophysiology device, the electrophysiology device including a shaft carrying at least one operative element, the suction device comprising:
a main body, a suction line extending through the main body;
two longitudinally spaced suction pods, a suction region being defined within each suction pod and being connected to the suction line through respective suction apertures defined by respective suction pods; and
a connector configured to removably secure the shaft of the electrophysiology device to the suction device such that the shaft extends through the suction regions, and a majority of the operative element carried by the shaft is between the suction regions.

14. A suction device as claimed in claim 13, the suction line being configured to be connected to a suction source.

15. A suction device as claimed in claim 13, wherein the suction pods comprise flexible suction pods.

16. A suction device as claimed in claim 13, wherein the connector comprises a slot.

17. A suction device as claimed in claim 13, wherein the connector is configured to removably secure a shaft of an electrophysiology device to the suction device such that the shaft extends through the suction regions, and respective portions of the shaft located between longitudinally spaced operative elements carried on the shaft are aligned within respective suction regions defined by the suction pods.

18. A system, comprising:
an electrophysiology device including a support structure carrying at least one operative element and defining an internal fluid lumen and a fluid outlet; and
a suction device including
a main body, a suction line extending through the main body,
at least one suction pod, a suction region being defined within the at least one suction pod and being connected to the suction line through a suction aperture formed through the at least one suction pod, and
a connector that removably secures the support structure to the suction device;
wherein the electrophysiology device and suction device are respectively configured such that the support structure extends through the suction region, and the fluid outlet defined by the support structure is within the suction region.

19. A system as claimed in claim 18, wherein the electrophysiology device defines a distal end, the connector comprises a slot defining a distal end, and the electrophysiology device and suction device are respectively configured such that the fluid outlet is within the suction region when the distal end of the electrophysiology device is adjacent to the distal end of the slot.

20. A system as claimed in claim 18, wherein the at least one suction pod comprises a plurality of suction pods, a suction region being defined within each suction pod, the support structure extending through a plurality of suction regions.

21. A system as claimed in claim 18, wherein the suction line is configured to be connected to a suction source.

22. A system as claimed in claim 18, wherein the suction device comprises a flexible suction device.

23. A system as claimed in claim 18, wherein the support structure of the electrophysiology device includes a plurality of fluid outlets, the at least one suction pod comprises a plurality of suction pods, each suction pod defining a respective suction region within a suction pod, and the electrophysiology device and suction device are respectively configured such that the support structure extends through a plurality of suction regions and each fluid outlet is within a respective suction region when the electrophysiology device is connected to the suction device.

24. A system as claimed in claim 18, wherein the at least one operative element comprises a plurality of spaced electrodes.

25. A system, comprising:
an electrophysiology device including a support structure and at least one operative element carried on the support structure; and
a suction device including a main body, a suction line extending through the main body, at least one suction pod defining a bottom surface, a suction region being defined within the at least one suction pod, and a connector that removably secures the support structure of the electrophysiology device to the suction device; wherein the electrophysiology device and suction device are respectively configured such that the support structure extends through the suction region, and a portion of the electrophysiology device within the suction region extends below the bottom surface of the suction pod when the electrophysiology device is connected to the suction device.

26. A system as claimed in claim 25, wherein the electrophysiology device and connector are configured such that the portion of the electrophysiology device extends about 0.5 mm below the bottom surface of the suction pod when the electrophysiology device is connected to the suction device.

27. A system as claimed in claim 25, wherein the at least one suction pod comprises a plurality of suction pods, a suction region being defined within each suction pod, the support structure extending through a plurality of suction regions.

28. A system as claimed in claim 25, wherein the suction line is configured to be connected to a suction source.

29. A system as claimed in claim 25, wherein the suction devices comprises a flexible suction device.

30. A system as claimed in claim 25, wherein the at least one operative element comprises a plurality of spaced electrodes.

31. A system, comprising:
an electrophysiology device including a support structure and at least one operative element carried on the support structure; and
a suction device including
a main body, a suction line extending through the main body,
two longitudinally spaced suction pods, a suction region being defined within each suction pod and being connected to the suction line through a suction aperture defined by a suction pod, and
a connector configured to removably secure the electrophysiology device to the suction device;
wherein the electrophysiology device and suction device are respectively configured such that the support structure extends through the suction regions, and a majority of the operative element is between the suction regions of respective suction pods when the electrophysiology device is connected to the suction device.

32. A system as claimed in claim 31, the suction line being configured to be connected to a suction source.

33. A system as claimed in claim 31, wherein the suction device comprises a flexible suction device.

34. A system as claimed in claim 31, wherein the support structure of the electrophysiology device includes a plurality of longitudinally spaced operative elements-and the electrophysiology device and suction device are respectively configured such that respective portions of the support body between the longitudinally spaced operative elements are aligned with suction regions defined by the suction pods when the electrophysiology device is connected to the suction device.

35. A system as claimed in claim 31, wherein the plurality of longitudinally spaced operative elements comprises a plurality of longitudinally spaced electrodes.

36. A system as claimed in claim 31, further comprising:
a suction source adapted to be operably connected to the suction device.

37. A method of operating an electrophysiology device, the electrophysiology device including a support structure carrying at least one operative element, and defining an internal fluid lumen and a least one fluid outlet, the method comprising the steps of:
securing a portion of the support structure to tissue with a suction device such that the support structure extends through a suction region of the suction device;
supplying cooling fluid through the internal fluid lumen of the support structure; and
drawing fluid from the at least one fluid outlet of the support structure and into the suction device.

38. A method as claimed in claim 37, further comprising the step of removably securing the suction device to the electrophysiology device by creating an interference fit between the suction device and the electrophysiology device.

39. A method as claimed in claim 37, further comprising the step of: performing at least one of a diagnostic and a therapeutic procedure after the support structure is secured to tissue with the suction device.

40. A method as claimed in claim 37, wherein the support structure of the electrophysiology device includes a plurality of fluid outlets; and the step of drawing fluid comprises drawing fluid from each fluid outlet of the plurality of fluid outlets into the suction device.

41. A method as claimed in claim 37, further comprising the step of: removing the fluid drawn into the suction device from a patient.

42. A method of operating an electrophysiology device, the electrophysiology device including a support structure, at least one operative element carried on the support structure, a fluid lumen and a fluid outlet, the method comprising the steps of:
securing a portion of the support structure to tissue with a suction device;
supplying cooling fluid to the fluid lumen;
drawing fluid from the fluid outlet into the suction device; and
vaporizing the fluid.

* * * * *